US008906882B2

(12) United States Patent
Yedgar

(10) Patent No.: US 8,906,882 B2
(45) Date of Patent: *Dec. 9, 2014

(54) LIPID CONJUGATES IN THE TREATMENT OF ALLERGIC RHINITIS

(75) Inventor: Saul Yedgar, Jerusalem (IL)

(73) Assignee: Yissum Research Development Company of The Hebrew University of Jerusalem, Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/316,592

(22) Filed: Dec. 12, 2011

(65) Prior Publication Data

US 2012/0083466 A1  Apr. 5, 2012

Related U.S. Application Data

(63) Continuation-in-part of application No. 11/285,375, filed on Nov. 23, 2005, now Pat. No. 8,076,312, which is a continuation-in-part of application No. PCT/IL2005/001225, filed on Nov. 17, 2005, application No. 13/316,592, which is a continuation-in-part of application No. 12/463,792, filed on May 11, 2009, now abandoned, and a continuation-in-part of application No. 12/997,014, filed as application No. PCT/US2010/034317 on May 11, 2010.

(60) Provisional application No. 61/177,083, filed on May 11, 2009.

(51) Int. Cl.
  *A61K 31/685* (2006.01)
  *A61K 31/728* (2006.01)
  *A61K 31/727* (2006.01)
  *A61K 31/717* (2006.01)

(52) U.S. Cl.
  CPC ............ *A61K 31/685* (2013.01); *A61K 31/728* (2013.01); *A61K 31/727* (2013.01); *A61K 31/717* (2013.01)
  USPC .................. 514/56; 514/57; 514/59; 514/60; 514/114

(58) Field of Classification Search
  None
  See application file for complete search history.

(56) References Cited

U.S. PATENT DOCUMENTS

| | | | |
|---|---|---|---|
| 4,604,376 A | 8/1986 | Teng | |
| 4,624,919 A | 11/1986 | Kokusho et al. | |
| 4,654,327 A | 3/1987 | Teng | |
| 5,064,817 A | 11/1991 | Yedgar et al. | |
| 5,169,636 A | 12/1992 | Nanba et al. | |
| 5,354,853 A | 10/1994 | Staveski et al. | |
| 5,401,511 A | 3/1995 | Margalit | |
| 5,401,777 A | 3/1995 | Ammon et al. | |
| 5,464,942 A | 11/1995 | Sakurai et al. | |
| 5,470,578 A | 11/1995 | Aoki et al. | |
| 5,512,671 A | 4/1996 | Piantadosi et al. | |
| 5,587,363 A | 12/1996 | Henderson | |
| 5,707,821 A | 1/1998 | Rydel et al. | |
| 5,733,892 A | 3/1998 | Sakurai et al. | |
| 5,785,975 A | 7/1998 | Parikh | |
| 6,022,866 A | 2/2000 | Falk et al. | |
| 6,043,231 A | 3/2000 | Pruzanski et al. | |
| 6,071,532 A | 6/2000 | Chaikof et al. | |
| 6,162,787 A | 12/2000 | Sorgente et al. | |
| 6,171,614 B1 | 1/2001 | Chaikof et al. | |
| 6,180,596 B1 | 1/2001 | Tsao | |
| 6,325,385 B1 | 12/2001 | Iwashita et al. | |
| 6,749,813 B1 | 6/2004 | David et al. | |
| 7,034,006 B2 | 4/2006 | Yedgar et al. | |
| 7,101,859 B2 | 9/2006 | Yedgar et al. | |
| 7,141,552 B2 | 11/2006 | Yedgar et al. | |
| 7,393,938 B2 | 7/2008 | Yedgar | |
| 7,504,384 B2 | 3/2009 | Yedgar et al. | |
| 7,608,598 B2 | 10/2009 | Yedgar | |
| 2002/0049183 A1 | 4/2002 | Yedgar et al. | |
| 2004/0087492 A1 | 5/2004 | Yedgar | |
| 2004/0229842 A1 | 11/2004 | Yedgar et al. | |

FOREIGN PATENT DOCUMENTS

| | | |
|---|---|---|
| EP | 0236951 | 9/1987 |
| EP | 0529659 | 3/1993 |
| EP | 0581281 | 2/1994 |
| EP | 0581282 B | 2/1994 |
| EP | 1046394 | 10/2000 |
| JP | 04082893 | 3/1992 |
| JP | 09030979 | 2/1997 |
| JP | 2002345455 | 12/2002 |
| JP | 2003160498 | 3/2003 |
| JP | 2003335801 | 11/2003 |
| JP | 2004018841 | 1/2004 |
| JP | 2004170194 | 6/2004 |
| WO | WO 87/02777 | 5/1987 |
| WO | WO 91/00289 | 1/1991 |
| WO | WO 96/04001 | 2/1996 |

(Continued)

OTHER PUBLICATIONS

Mexican Office Action for Mexican Patent Application No. MX/a2008/001639 dated May 2, 2013.

Ehehalt, R. et al., "Lipid Based Therapy for Ulcerative Colitis—Modulation of Intestinal Mucus Membrane Phospholipids as a Tool to Influence Inflammation," Int. J. Mol. Sci. 2010, 11, 4149-4164.

Office Action for Japanese Patent Application No. 2001-551427 dated Nov. 20, 2009.

Extended European Search Report of European Application No. 05808267.8 issued Mar. 15, 2012.

(Continued)

*Primary Examiner* — Kamal Saeed
(74) *Attorney, Agent, or Firm* — Mark S. Cohen; Pearl Cohen; Zedek Latzer Baratz LLP

(57) ABSTRACT

Provided herein are methods of treating, suppressing, inhibiting, or preventing allergic rhinitis in a subject comprising the step of administering to a subject a compound comprising a lipid or phospholipid moiety bond to a physiologically acceptable monomer, dimer, oligomer, or polymer, and/or a pharmaceutically acceptable salt or a pharmaceutical product thereof.

17 Claims, 9 Drawing Sheets

(56) References Cited

FOREIGN PATENT DOCUMENTS

| WO | WO 96/11670 | 4/1996 |
|---|---|---|
| WO | WO 96/28544 | 9/1996 |
| WO | WO 97/01330 | 1/1997 |
| WO | WO 97/48337 | 12/1997 |
| WO | WO 98/016198 | 4/1998 |
| WO | WO 98/51285 | 11/1998 |
| WO | WO 01/51003 | 7/2001 |
| WO | WO 01/91805 | 12/2001 |
| WO | WO 2005/084307 | 9/2005 |

OTHER PUBLICATIONS

Phyllis, Dan et al., "Inhibition of Type I and Type II Phospholipase A2 by Phosphatidyl-Ethanolamine Linked to Polymeric Carriers," Biochemistry, 1998, 37 (17), pp. 6199-6204.
Albini, A, Iwamoto, Y, Kleinman, HK, Martin, GR, Aaronson, SA, Kozlowski, JM and McEwan, RN (1987) "A rapid in vitro assay for quantitating the invasive potential of tumor cells" Cancer Res 47(12):3239-45.
Balsinde, J, Balboa, MA, Yedgar, S and Dennis, EA (2000) "Group V phospholipase A(2)-mediated oleic acid mobilization in lipopolysaccharide-stimulated P388D(1) macrophages" J Biol Chem 275(7):4783-6.
Beck, G, Yard, BA, Schulte, J, Oberacker, R, Van Ackern, K, Van Der Woude, FJ, Krimsky, M, Kaszkin, M and Yedgar, S (2002) "Inhibition of LPS-induced chemokine production in human lung endothelial cells by lipid conjugates anchored to the membrane" Br J Pharmacol 135(7):1665-74.
Cabanas, C and Hogg, N (1993) "Ligand intercellular adhesion molecule 1 has a necessary role in activation of integrin lymphocyte function-associated molecule 1" Proc Natl Acad Sci U S A 90(12):5838-42.
Chen, WM, Soria, J, Soria, C, Krimsky, M and Yedgar, S (2002) "Control of capillary formation by membrane-anchored extracellular inhibitor of phospholipase A(2)" FEBS Lett 522(1-3):113-8.
Dan, P, Dagan, A, Krimsky, M, Pruzanski, W, Vadas, P and Yedgar, S (1998) "Inhibition of type I and type II phospholipase A2 by phosphatidyl-ethanolamine linked to polymeric carriers" Biochemistry 37(17):6199-204.
Darville, T, Yedgar, S, Krimsky, M, Andrews, CW, Jr., Jungas, T and Ojcius, DM (2004) "Protection against Chlamydia trachomatis infection in vitro and modulation of inflammatory response in vivo by membrane-bound glycosaminoglycans" Microbes Infect 6(4):369-76.
Greaves MW and Camp RD (1988) "Prostaglandins, leukotrienes, phospholipase, platelet activating factor, and cytokines: an integrated approach to inflammation of human skin." Arch Dermatol Res 280:S33-41.
Krimsky, M, Dagan, A, Aptekar, L, Ligumsky, M and Yedgar, S (2000) "Assessment of intestinal permeability in rats by permeation of inulin-fluorescein" J Basic Clin Physiol Pharmacol 11(2):143-53.
Krimsky, M, Yedgar, S, Aptekar, L, Schwob, O, Goshen, G, Gruzman, A, Sasson, S and Ligumsky, M (2003) "Amelioration of TNBS-induced colon inflammation in rats by phospholipase A2 inhibitor" Am J Physiol Gastrointest Liver Physiol 285(3):G586-92.
Margolis-Nunno, H, Ben-Hur, E, Gottlieb, P, Robinson, R, Oetjen, J and Horowitz, B (1996) "Inactivation by phthalocyanine photosensitization of multiple forms of human immunodeficiency virus in red cell concentrates" Transfusion 36(8):743-50.
Murthy, SN, Cooper, HS, Shim, H, Shah, RS, Ibrahim, SA and Sedergran, DJ (1993) "Treatment of dextran sulfate sodium-induced murine colitis by intracolonic cyclosporin" Dig Dis Sci 38(9):1722-34.
Okayasu, I, Hatakeyama, S, Yamada, M, Ohkusa, T, Inagaki, Y and Nakaya, R (1990) "A novel method in the induction of reliable experimental acute and chronic ulcerative colitis in mice" Gastroenterology 98(3):694-702.
Schmiel, DH and Miller, VL (1999) "Bacterial phospholipases and pathogenesis" Microbes Infect 1(13):1103-12.
Schnitzer, E, Dagan, A, Krimsky, M, Lichtenberg, D, Pinchuk, I, Shinar, H and Yedgar, S (2000) "Interaction of hyaluronic acid-linked phosphatidylethanolamine (HyPE) with LDL and its effect on the susceptibility of LDL lipids to oxidation" Chem Phys Lipids 104(2):149-60.
Schnitzer, E, Yedgar, S, Danino, D, Talmon, Y and Lichtenberg, D (1999) "The Interaction of hyaluronic-phosphatidylethanolamine with low density lipoprotein (LDL) and its effect on copper induced LDL oxidation" Biophysical Journal 76(1): Part 2.
Schnitzer, E, Pinchuk, I, Fainaru, M, Lichtenberg, D and Yedgar, S (1998) "LDL-associated phospholipase A does not protect LDL against lipid peroxidation in vitro" Free Radic Biol Med 24(7-8):1294-303.
Yard, BA, Yedgar, S, Scheele, M, Van Der Woude, D, Beck, G, Heidrich, B, Krimsky, M, Van Der Woude, FJ and Post, S (2002) "Modulation of IFN-gamma-induced immunogenicity by phosphatidylethanolamine-linked hyaluronic acid" Transplantation 73(6):984-92.
Yedgar, S, Lichtenberg, D and Schnitzer, E (2000) "Inhibition of phospholipase A(2) as a therapeutic target" Biochim Biophys Acta 1488(1-2):182-7.
Soeda et al., "Tissue Plasminogen Activator Catalyzed Lys-Plasminogen Activation on Heparin-Inserted Phospholipid Liposomes," Biochemistry 29:5188-5194, 1990.
Teitelbaum D, Arnon R, Sela M, Rabinsohn Y, Shapiro D., "Sphingomyelin Specific Antibodies Elicited by Synthetic Conjugates," Immunochemistry. Nov. 1973;10(11):735-43.
Weltzien HU, Matthiessen HP, Meyer-Delius M, Zimmermann F, Rüde E., "Acidic Peptidophospholipids", A New Class of Hapten-Bearing Cell Surface Modifying Reagents, Mol Immunol. Sep. 1984;21(9):801-10.
Winger TM, Ludovice PJ, Chaikof EL, "Lipopeptide Conjugates: Biomolecular Building Blocks for Receptor Activating Membrane-Mimetic Structures," Biomaterials. Feb. 1996;17(4):437-41.
Supplementary Search Report of European Application No. 05724186.1 Dated Nov. 17, 2009.
Cummings, B.S., "Phospholipase $A_2$ as targets for anti-cancer drugs," Biochemical Pharmacology 74 (2007), pp. 949-959.
Kokotos, G. et al., "Novel 2-Oxoamide Inhibitors of Human Group IVA Phospholipase $A_2$," J. Med. Chem., 2002, 45, pp. 2891-2893.
Brenner, T, Arnon, R, Sela, M, Abramsky, O, Meiner, Z, Riven-Kreitman, R, Tarcik, N and Teitelbaum, D (2001) "Humoral and cellular immune responses to Copolymer 1 in multiple sclerosis patients treated with Copaxone" J Neuroimmunol 115(1-2):152-60.
Brenner, T, Lisak, RP, Rostami, A, Pleasure, DE and Silberberg, DH (1986) "Astrocytes, oligodendrocytes, and Schwann cells share a common antigenic determinant that cross-reacts with myelin basic protein: Identification with monoclonal antibody" J Neurosci 6(7):1925-33.
Brenner, T, Poradosu, E, Soffer, D, Sicsic, C, Gazit, A and Levitzki, A (1998) "Suppression of experimental autoimmune encephalomyelitis by tyrphostin AG-556" Exp Neurol 154(2):489-98.
Carey et al, "Contrasting Effects of Cycloxygenase-1 (COX-1) and COX-2 Deficiency in the Host Response to Influenza, a Viral Infection". Journ. of Immunology 2005, vol. 15: 175 (10): 6878-84.
Davidson, FF, Dennis, EA, Powell, M and Glenney, JR, Jr. (1987) "Inhibition of phospholipase A2 by "lipocortins" and calpactins. An effect of binding to substrate phospholipids" J Biol Chem 262(4):1698-705.
Parish et al, "Evidence That Sulphated Polysaccharides Inhibit Tumour Metastasis by Blocking Tumour-Cell-Derived Heparanases," Int. J. Cancer 40: 511-518, 1987.
Wang D.P, Matthias Schuster, Yi Fong Wang, Chi Huey Wong "Synthesis of Phospholipid-Inhibitor Conjugates by Enzymic Transphosphatidylation with Phospholipase", J. Am. Chem. Soc.; 1993; 115(23); 10487-10491.

ic rhinitis is one of the most common global chronic diseases, affecting at least 10% to 25% of the population and its prevalence is increasing. Symptoms of AR can cause fatigue, headache, cognitive impairment and other systemic symptoms and may significantly impact a patient's quality of life. Appropriate management of AR may also be an important component in effective management of coexisting or complicating respiratory conditions, such as asthma, sinusitis, or chronic otitis media.
LIPID CONJUGATES IN THE TREATMENT OF ALLERGIC RHINITIS

CROSS REFERENCE TO RELATED APPLICATIONS

This application is a continuation-in-part of U.S. application Ser. No. 11/285,375, filed Nov. 23, 2005, now U.S. Pat. No. 8,076,312, which is a continuation-in-part of PCT International Application Number PCT/IL2005/001225, filed Nov. 17, 2005. This application is also a continuation-in-part of U.S. application Ser. No. 12/463,792, filed May 11, 2009 now abandoned, and of U.S. application Ser. No. 12/997,014, filed Dec. 9, 2010, which is a National Phase Application of PCT International Application No. PCT/US10/34317, International Filing Date May 11, 2010, claiming priority of U.S. Provisional Application No. 61/177,083, filed May 11, 2009, which are all hereby incorporated by reference in their entirety.

FIELD OF THE INVENTION

Provided herein are method of treating, suppressing, inhibiting, or preventing allergic rhinitis in a subject comprising the step of administering to a subject a compound comprising a lipid or phospholipid moiety bond to a physiologically acceptable monomer, dimer, oligomer, or polymer, and/or a pharmaceutically acceptable salt or a pharmaceutical product thereof.

BACKGROUND OF THE INVENTION

Lipid-conjugates having a pharmacological activity of inhibiting the enzyme phospholipase A2 (PLA2, EC 3.1.1.4) are known in the prior art. Phospholipase A2 catalyzes the breakdown of phospholipids at the sn-2 position to produce a fatty acid and a lysophospholipid. The activity of this enzyme has been correlated with various cell functions, particularly with the production of lipid mediators such as eicosanoid production (prostaglandins, thromboxanes and leukotrienes), platelet activating factor and lysophospholipids.

Glycosaminoglycans (GAG) are macro-molecules that protect the cell membrane from attacks or stimuli by a multitude of extra-cellular agents such as: Free radicals (ROS), exogenous PLA2, interleukins and other inflammatory mediators, allergens, growth factors, and degrading enzymes or invasion-promoting enzymes (e.g., heparinase, collagenase, heparanase, hyaluronidase). GAG enrichment assists in protecting cells from damage.

Since their inception, lipid-conjugates have been subjected to intensive laboratory investigation in order to obtain a wider scope of protection of cells and organisms from injurious agents and pathogenic processes.

Allergic rhinitis (AR) is an allergen-induced inflammation of the membranes lining the nose. Exposure to the allergen in AR stimulates the release of histamine and other inflammatory mediators, which cause a collection of symptoms, including nasal congestion, rhinorrhea, frontal headache, post-nasal drip, sneezing, nasal itch, itching in the ears or palate, and cough.

Allergic rhinitis is one of the most common global chronic diseases, affecting at least 10% to 25% of the population and its prevalence is increasing. Symptoms of AR can cause fatigue, headache, cognitive impairment and other systemic symptoms and may significantly impact a patient's quality of life. Appropriate management of AR may also be an important component in effective management of coexisting or complicating respiratory conditions, such as asthma, sinusitis, or chronic otitis media.

Among the goals of allergy treatment is to prevent the release of inflammatory mediators and thereby mitigate the symptoms associated with inflammation. Current treatment approaches for AR involve a step-wise approach dependent on the frequency and severity of symptoms. The most common treatments include H1-antihistamines, decongestants, mast cell stabilizers (cromones), anticholinergics, antileukotrienes, and intranasal corticosteroids (INS); these treatments vary in both mechanism and effectiveness.

SUMMARY OF THE INVENTION

In one aspect, methods are provided for treating allergic rhinitis in a subject comprising the step of administering to said subject a compound represented by the structure of the general formula (A):

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000.

In another aspect, methods are provided for preventing allergic rhinitis in a subject, comprising the step of administering to said subject a compound represented by the structure of the general formula (A):

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000.

In certain embodiments, X in general formula (A) is a polysaccharide. In some embodiments, the polysaccharide is carboxymethylcellulose, while in other embodiments, the polysaccharide is a glycosaminoglycan. In some embodiments, the glycosaminoglycan is hyaluronic acid, while in other embodiments, the glycosaminoglycan is heparin. In certain embodiments, L in general formula (A) is phosphatidylethanolamine, which in some embodiments is dipalmitoyl phosphatidylethanolamine.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description. It is also contemplated that whenever appropriate, any embodiment of the present invention can be combined with one or more other embodiments of the present invention, even

DETAILED DESCRIPTION OF THE INVENTION

Figure 1:
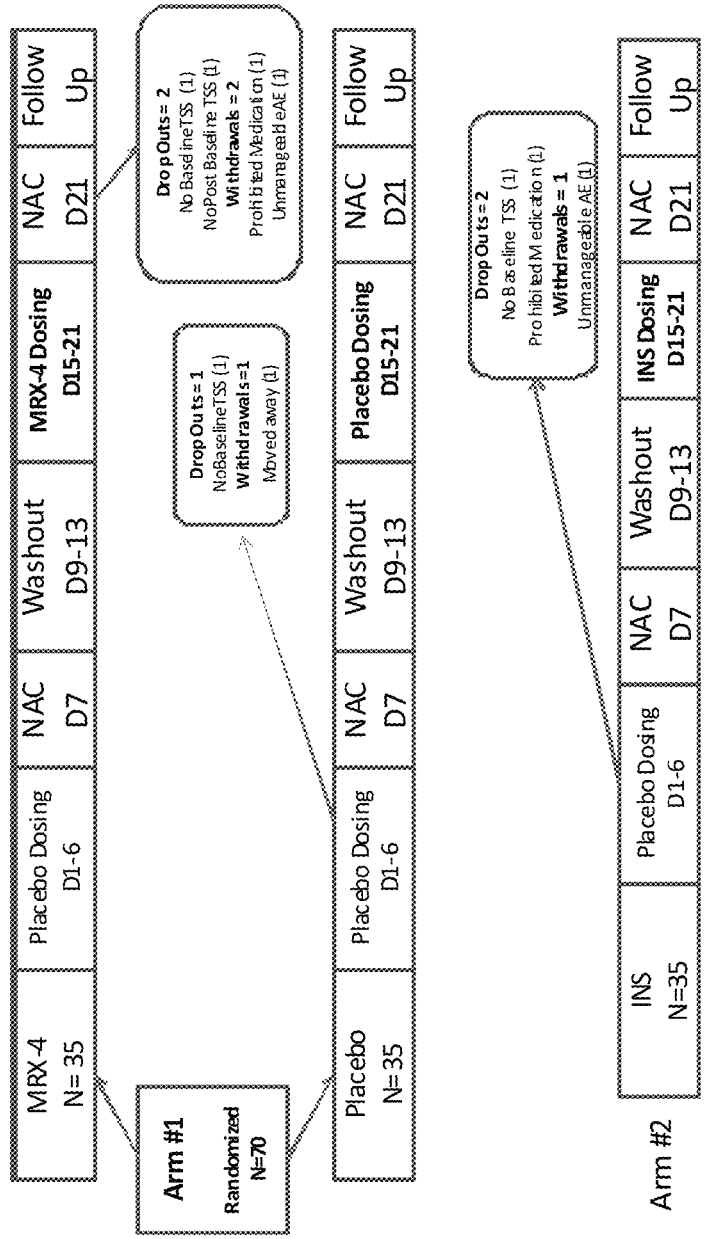
FIG. 1 depicts the study design of the clinical trial described in Example 1.
Figure 2:
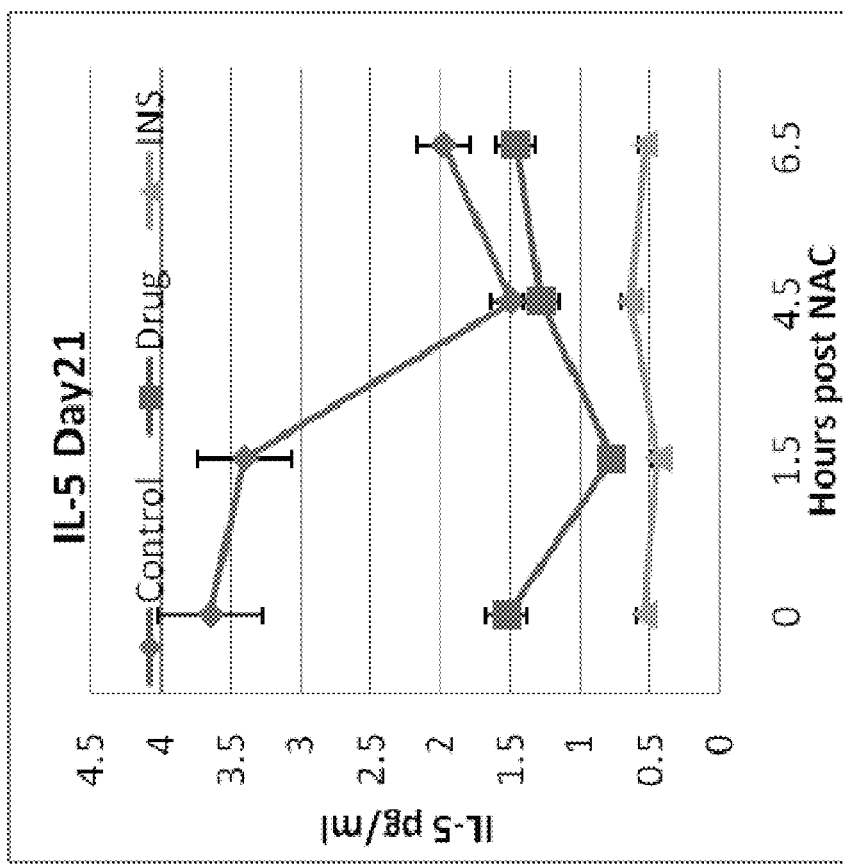
FIG. 2. Plots of the mean (normalised) IL-5 levels at Day 21 for the Placebo, HyPE (Drug) and steroid (INS) groups, respectively.
Figure 3:
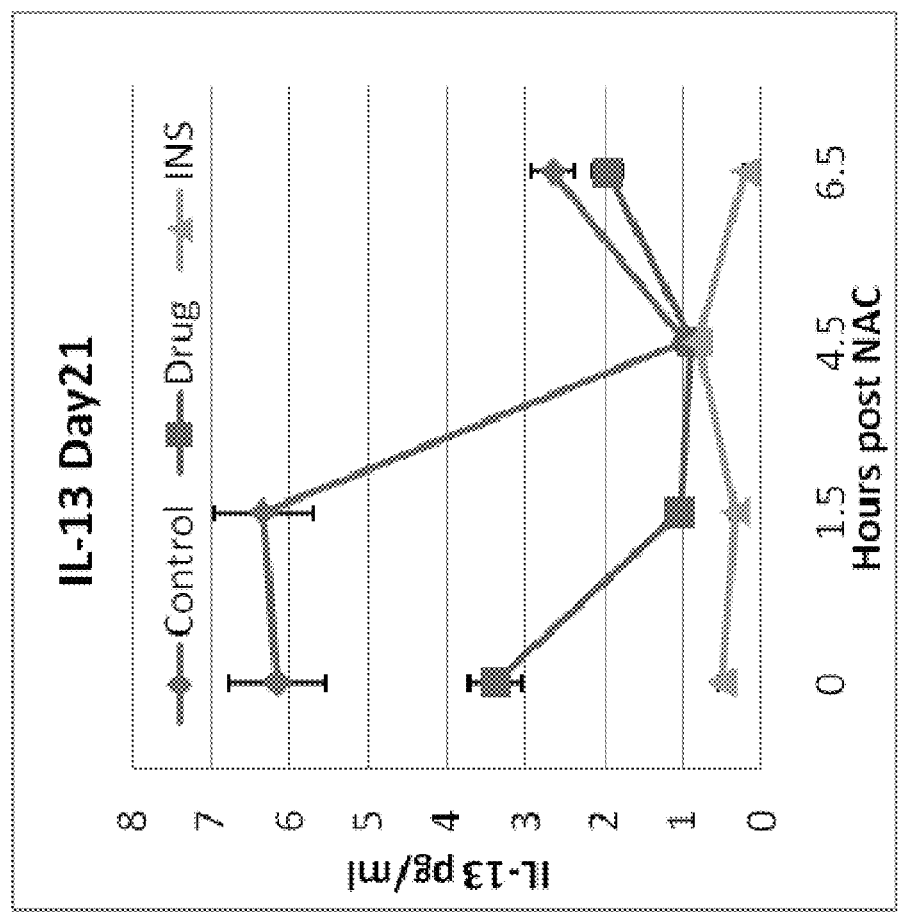
FIG. 3. Plots of the mean (normalised) IL-13 levels at Day 21 for the Placebo, HyPE (Drug) and steroid (INS) groups, respectively.
Figure 4:
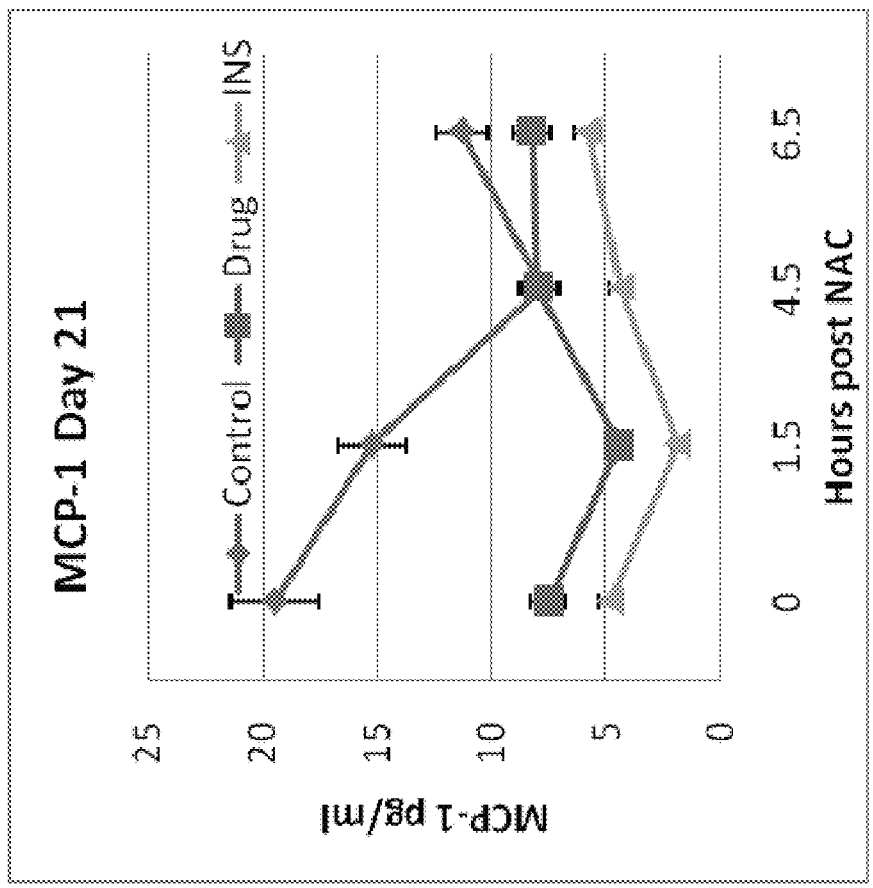
FIG. 4. Plots of the mean (normalised) MCP-1 levels at Day 21 for the Placebo, HyPE (Drug) and steroid (INS) groups, respectively.
Figure 5:
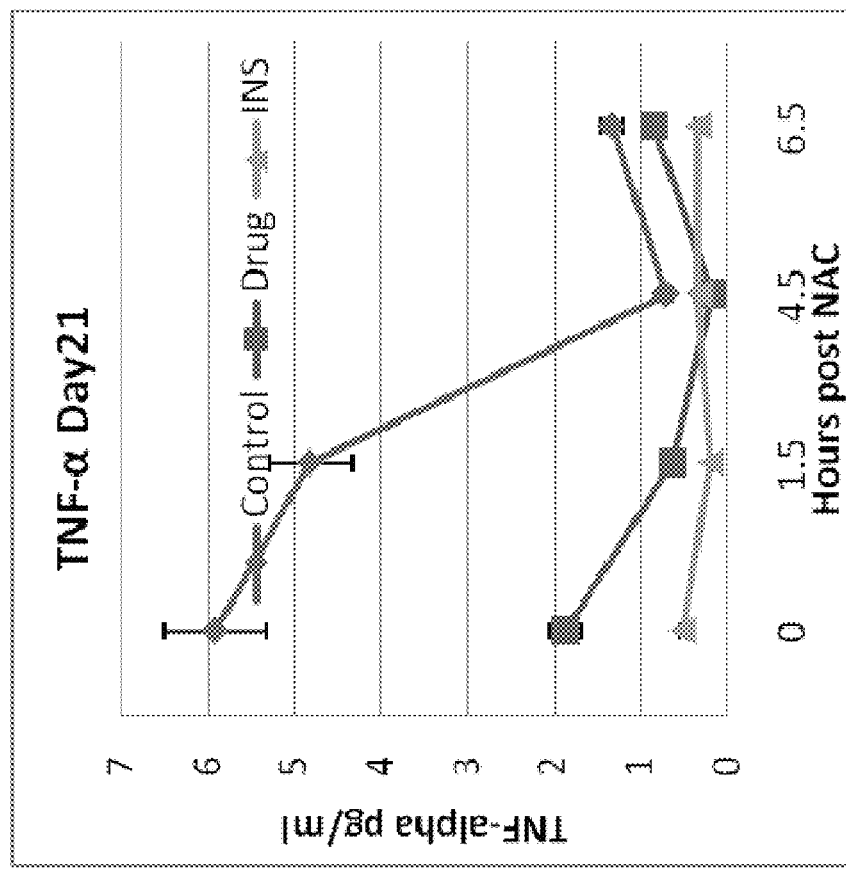
FIG. 5. Plots of the mean (normalised) TNF-α levels at Day 21 for the Placebo, HyPE (Drug) and steroid (INS) groups, respectively.
Figure 6:
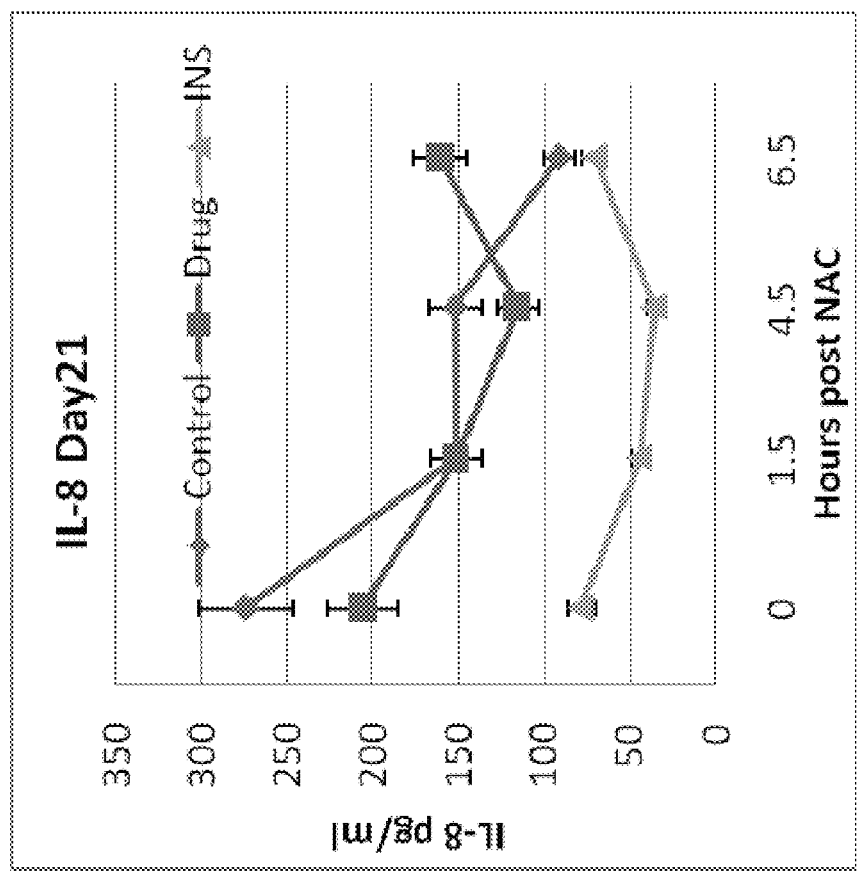
FIG. 6. Plots of the mean (normalised) IL-8 levels at Day 21 for the Placebo, HyPE (Drug) and steroid (INS) groups, respectively.
Figure 7:
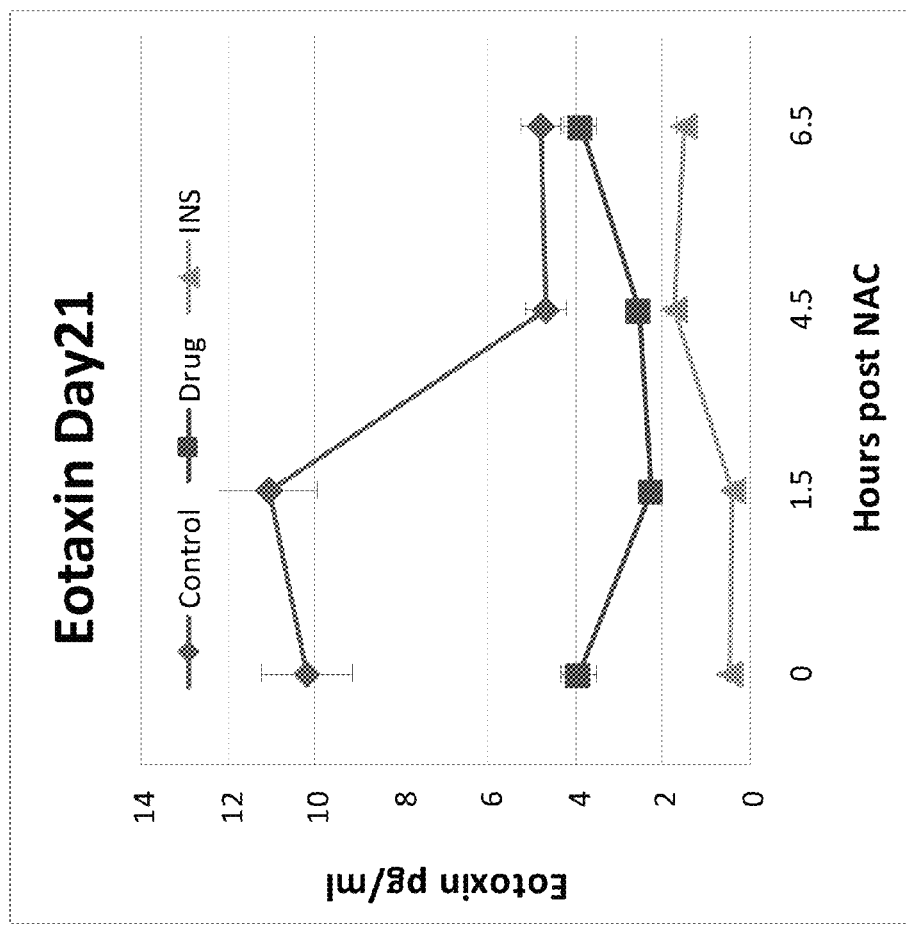
FIG. 7. Plots of the mean (normalised) Eotaxin levels at Day 21 for the Placebo, HyPE (Drug) and steroid (INS) groups, respectively.
Figure 8:
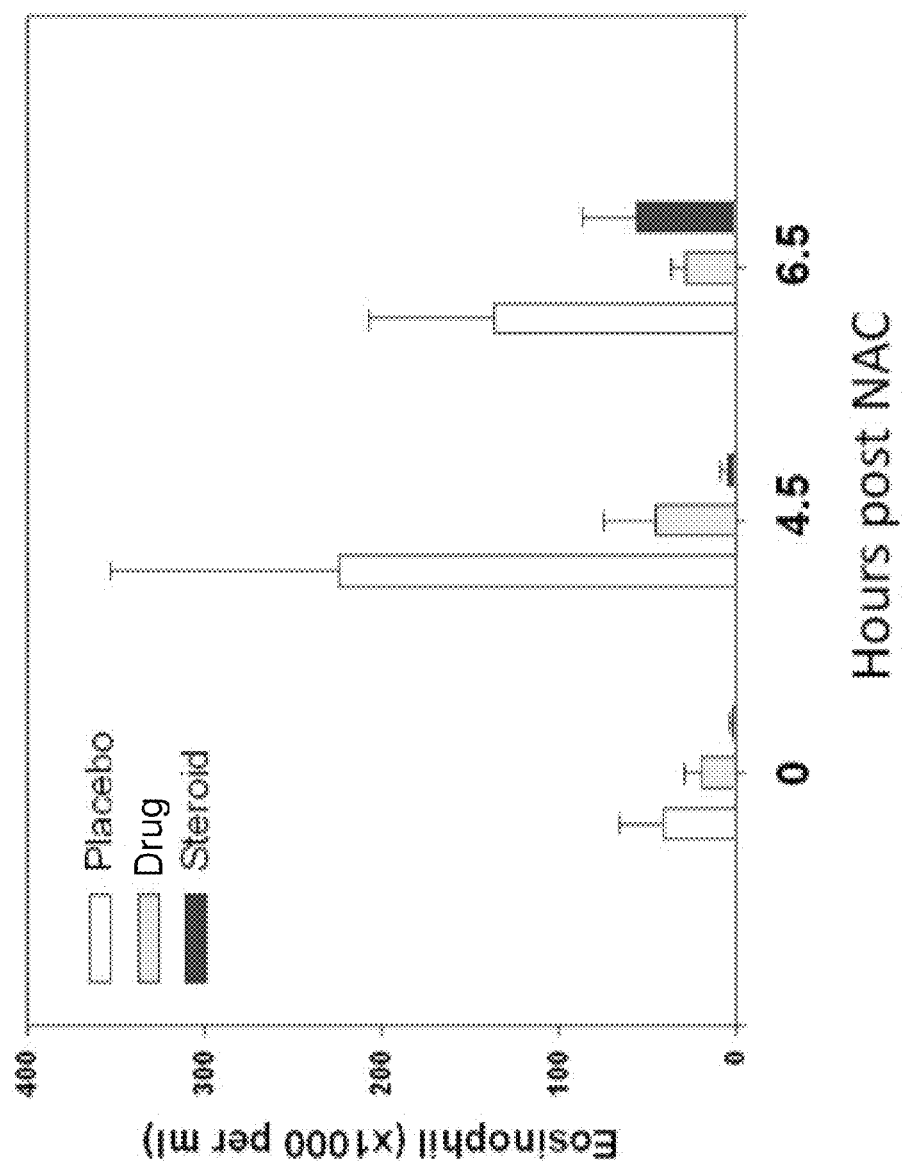
FIG. 8. Plots of the mean (normalised) eosinophils at Day 21 for the Placebo, HyPE (Drug) and steroid (INS) groups, respectively.

Disclosed herein are novel methods of use for lipid-conjugates which display a wide-range combination of cytoprotective pharmacological activities. These compounds can alleviate airway obstruction in asthma, protect mucosal tissue in gastrointestinal disease, suppress immune responses, alleviate cutaneous hypersensitivity reactions, inhibit cell proliferation associated with vascular injury and immunological responses, inhibit cell migration associated with vascular and central nervous system disease, attenuate oxidative damage to tissue proteins and cell membranes, interfere with viral spread, reduce tissue destroying enzyme activity, and reduce intracellular levels of chemokines and cytokines. Thus these compounds are useful in the treatment of a diversity of disease states, including asthma, rhinitis, allergic rhinitis, chronic obstructive pulmonary disease, obstructive respiratory disease, colitis, Crohn's disease, central nervous system insult, multiple sclerosis, contact dermatitis, psoriasis, cardiovascular disease, invasive medical procedures, invasive cellular proliferative disorders, anti-oxidant therapy, hemolytic syndromes, sepsis, acute respiratory distress syndrome, tissue transplant rejection syndromes, autoimmune disease, viral infection, and hypersensitivity conjunctivitis.

In certain embodiments, methods are provided of treating an obstructive respiratory disease in a subject comprising the step of administering to said subject a compound represented by the structure of the general formula (A):

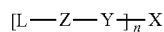  (A)

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000.

In certain embodiments, methods are provided of preventing an obstructive respiratory disease in a subject, comprising the step of administering to said subject a compound represented by the structure of the general formula (A):

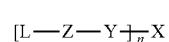  (A)

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000.

In certain of the foregoing embodiments, the obstructive respiratory disease is rhinosinusitis. In other embodiments, the obstructive respiratory disease comprises a physical or anatomical obstruction, which in some embodiments, is a nasal polyp. In some embodiments, the obstructive respiratory disease is rhinitis. In yet other embodiments, the obstructive respiratory disease is sinusitis. In certain other embodiments, the obstructive respiratory disease is asthma. In certain embodiments, the obstructive respiratory disease is allergic rhinitis. In certain other embodiments, the obstructive respiratory disease is chronic obstructive pulmonary disorder. In yet further embodiments, the obstructive respiratory disease is nasal polyposis.

In certain embodiments, methods are provided for treating allergic rhinitis in a subject comprising the step of administering to said subject a compound represented by the structure of the general formula (A):

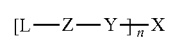  (A)

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000.

In certain embodiments, methods are provided for preventing allergic rhinitis in a subject, comprising the step of administering to said subject a compound represented by the structure of the general formula (A):

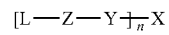  (A)

wherein
L is a lipid or a phospholipid;

Z is either nothing, ethanolamine, serine, inositol, choline, or glycerol;

Y is either nothing or a spacer group ranging in length from 2 to 30 atoms;

X is a physiologically acceptable monomer, dimer, oligomer, or polymer; and n is a number from 1 to 1000.

In certain embodiments, X in general formula (A) is a polysaccharide. In some embodiments, the polysaccharide is carboxymethylcellulose, while in other embodiments, the polysaccharide is a glycosaminoglycan. In some embodiments, the glycosaminoglycan is hyaluronic acid, while in other embodiments, the glycosaminoglycan is heparin. In certain embodiments, L in general formula (A) is phosphatidylethanolamine, which in some embodiments is dipalmitoyl phosphatidylethanolamine.

In certain embodiments, the invention provides for the use of a compound represented by the structure of the general formula (A):

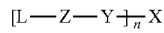
(A)

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000
for the preparation of a composition to treat allergic rhinitis.

In certain embodiments, the invention provides for the use of a compound represented by the structure of the general formula (A):

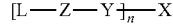
(A)

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000
for the preparation of a composition to prevent allergic rhinitis.

In certain embodiments, the invention provides for the use of a compound represented by the structure of the general formula (A):

(A)

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000
for treating allergic rhinitis.

In certain embodiments, the invention provides for the use of a compound represented by the structure of the general formula (A):

(A)

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000
for preventing allergic rhinitis.

In certain embodiments, compositions of the present invention may be used to treat, suppress, inhibit or prevent rhinosinusitis initially caused by a stimulus, such as an allergen, environmental stimulus, fungus, bacteria, or virus. In some embodiments, the bacterial infection is *Staphylococcus Aureus*. In some embodiments, the fungus or bacteria colonizes the sinus thereby causing an aggressive inflammatory reaction. In further embodiments, any of the stimuli described hereinabove leads to an inflammatory reaction of rhinosinusitis.

In certain embodiments, the invention provides methods of decreasing cytokine levels in a subject, comprising the step of administering to said subject a compound of the present invention. In some embodiments, the invention provides methods of returning elevated cytokine levels to basal levels in a subject, comprising the step of administering to said subject a compound of the present invention. In another embodiment, the invention provides methods of decreasing IL-13 levels in a subject, comprising the step of administering to said subject a compound of the present invention. In another embodiment, the invention provides methods of decreasing IL-5 levels in a subject, comprising the step of administering to said subject a compound of the present invention. In another embodiment, the invention provides methods of decreasing MCP-1 levels in a subject, comprising the step of administering to said subject a compound of the present invention. In another embodiment, the invention provides methods of decreasing TNF-α levels in a subject, comprising the step of administering to said subject a compound of the present invention. In another embodiment, the invention provides methods of decreasing IL-8 levels in a subject, comprising the step of administering to said subject a compound of the present invention. In another embodiment, the invention provides methods of decreasing eotaxin levels in a subject, comprising the step of administering to said subject a compound of the present invention. In another embodiment, the invention provides methods of decreasing interferon-γ levels in a subject, comprising the step of administering to said subject a compound of the present invention. In another embodiment, the invention provides methods of reversing increased IL-13 levels in a subject, comprising the step of administering to said subject a compound of the present invention. In another embodiment, the invention provides methods of reversing increased IL-5 levels in a subject, comprising the step of administering to said subject a compound of the present invention. In another embodiment, the invention provides methods of reversing increased MCP-1 levels in a subject, comprising the step of administering to said subject a compound of the present invention. In another embodiment, the invention provides methods of reversing increased TNF-α levels in a subject, comprising the step of administering to said subject a compound of the present invention. In another embodiment, the invention provides methods of reversing increased IL-8 levels in a subject, comprising the step of administering to said subject a compound of the present invention. In another embodiment, the invention provides methods of reversing increased eotaxin levels in a subject, comprising the step of administering to said subject a compound of the present invention. In another embodiment, the invention provides methods of reversing increased interferon-γ levels in a subject, comprising the step of administering to said subject a compound of the present invention.

In certain embodiments, X in general formula (A) is a polysaccharide. In some embodiments, the polysaccharide is carboxymethylcellulose, while in other embodiments, the polysaccharide is a glycosaminoglycan. In some embodiments, the glycosaminoglycan is hyaluronic acid, while in other embodiments, the glycosaminoglycan is heparin. In certain embodiments, L in general formula (A) is phosphatidylethanolamine, which in some embodiments is dipalmitoyl phosphatidylethanolamine.

In some embodiments, "treating" or "preventing" refers to delaying the onset of symptoms, reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, preventing relapse to a disease, decreasing the number or frequency of relapse episodes, increasing latency between symptomatic episodes, increasing time to sustained progression, expediting remission, inducing remission, augmenting remission, speeding recovery, or increasing efficacy of or decreasing resistance to alternative therapeutics.

In some embodiments, the symptoms of allergic rhinitis treated and/or prevented include one or more of the following symptoms: nasal congestion, rhinorrhea, frontal headache, post-nasal drip, sneezing, nasal itch, itching ears/palate and cough. In certain embodiments the symptoms of allergic rhinitis treated and/or prevented include one or more of the following symptoms: nasal congestion, rhinorrhea, sneezing and nasal itch. In further embodiments, at least the symptom of coughing is treated and/or prevented; while, in other embodiments, at least the symptom of coughing is treated and/or prevented.

In some embodiments, treating and/or preventing allergic rhinitis includes reducing the level of one or more of the following cytokines: IL-5, IL-13, MCP-1, TNF-α, IL-8 and eotaxin. In certain embodiments, treating or preventing allergic rhinitis includes reducing eosinophil counts.

In some embodiments, symptoms are primary, while in other embodiments, symptoms are secondary. As used herein, "primary" refers to a symptom that is a direct result of infection with a pathogen or direct result of challenge with an antigen, while "secondary" refers to a symptom that is derived from or consequent to a primary cause.

In certain embodiments, the invention provides methods of treating a subject suffering from allergic rhinitis, comprising the step of administering to a subject a compound comprising a lipid or phospholipid moiety bond to a physiologically acceptable monomer, dimer, oligomer, or polymer, and/or a pharmaceutically acceptable salt or a pharmaceutical product thereof, in an amount effective to treat the subject suffering from allergic rhinitis. In some embodiments, the invention provides methods of treating a subject suffering from allergic rhinitis, comprising the step of administering to a subject any one of the compounds according to the invention, in an amount effective to treat the subject suffering from allergic rhinitis.

In certain embodiments, the invention provides methods of treating a subject suffering from an obstructive respiratory disease, comprising the step of administering to a subject a compound comprising a lipid or phospholipid moiety bond to a physiologically acceptable monomer, dimer, oligomer, or polymer, and/or a pharmaceutically acceptable salt or a pharmaceutical product thereof, in an amount effective to treat the subject suffering from an obstructive respiratory disease. In some embodiments, the invention provides methods of treating a subject suffering from an obstructive respiratory disease, comprising the step of administering to a subject any one of the compounds according to the invention, in an amount effective to treat the subject suffering from an obstructive respiratory disease. In another embodiment, the obstructive respiratory disease is asthma.

In certain embodiments of the present invention, the physiologically acceptable monomer is either a salicylate, salicylic acid, aspirin, a monosaccharide, lactobionic acid, maltose, an amino acid, glycine, carboxylic acid, acetic acid, butyric acid, dicarboxylic acid, glutaric acid, succinic acid, fatty acid, dodecanoic acid, didodecanoic acid, bile acid, cholic acid, cholesterylhemmisuccinate; or wherein the physiologically acceptable dimer or oligomer is a dipeptide, a disaccharide, a trisaccharide, an oligopeptide, or a di- or trisaccharide monomer unit of heparin, heparan sulfate, keratin, keratan sulfate, chondroitin, chondoitin sulfate, dermatin, dermatan sulfate, dextran, or hyaluronic acid; or wherein the physiologically acceptable polymer is a glycosaminoglycan, polygelin ('hemaccell'), alginate, hydroxyethyl starch (hetastarch), polyethylene glycol, polycarboxylated polyethylene glycol, chondroitin sulfate, keratin, keratin sulfate, heparan sulfate, dermatin, dermatan sulfate, carboxymethylcellulose, heparin, dextran, or hyaluronic acid. In some embodiments, the physiologically acceptable polymer is chondrotin sulfate. In some embodiments, the chondrotin sulfate is chondrotin-6-sulfate, chondroitin-4-sulfate or a derivative thereof. In some embodiments, the physiologically acceptable polymer is hyaluronic acid.

In certain embodiments of the invention, the lipid or phospholipid moiety is either phosphatidic acid, an acyl glycerol, monoacylglycerol, diacylglycerol, triacylglycerol, sphingosine, sphingomyelin, chondroitin-4-sulphate, chondroitin-6-sulphate, ceramide, phosphatidylethanolamine, phosphatidylserine, phosphatidylcholine, phosphatidylinositol, or phosphatidylglycerol, or an ether or alkyl phospholipid derivative thereof, and the physiologically acceptable monomer or polymer moiety is either aspirin, lactobionic acid, maltose, glutaric acid, polyethylene glycol, carboxymethylcellulose, heparin, dextran, hemacell, hetastarch, or hyaluronic acid. In some embodiments, the phospholipid moiety is phosphatidylethanolamine.

In certain embodiments, obstructive respiratory disease is a disease of luminal passages in the lungs, marked by dyspnea, tachypnea, or auscultatory or radiological signs of airway obstruction. Obstructive respiratory disease comprises asthma, acute pulmonary infections, acute respiratory distress syndrome, chronic obstructive pulmonary disease, rhinitis, and allergic rhinitis. In some embodiments, the pathophysiology is attributed to obstruction of air flow due to constriction of airway lumen smooth muscle and accumulation of infiltrates in and around the airway lumen.

In certain embodiments, asthma is a disease process wherein the bronchi may be narrowed, making breathing difficult. In some embodiments, symptoms comprise wheezing, difficulty breathing (particularly exhaling air), tightness in the chest, or a combination thereof. In some embodiments, factors which can exacerbate asthma include rapid changes in temperature or humidity, allergies, upper respiratory infections, exercise, stress, smoke (e.g., cigarette), or a combination thereof.

In certain embodiments, rhinitis comprises an inflammation of the mucous membrane of the nose. In some embodiments, allergic rhinitis is an inflammatory response in the nasal passages to an allergic stimulus. In certain embodiments, symptoms comprise nasal congestion, sneezing, runny, itchy nose, or a combination thereof.

In certain embodiments, chronic obstructive pulmonary disease is a progressive disease process that most commonly results from smoking. In some embodiments, chronic obstructive pulmonary disease comprises difficulty breathing, wheezing, coughing, which may be a chronic cough, or a combination thereof. In some embodiments, chronic obstructive pulmonary disease may lead to health complications, which in certain embodiments, may comprise bronchitis, pneumonia, lung cancer, or a combination thereof.

Cellular elaboration of cytokines and chemokines serve an important regulatory function in health; however, when a hyperactive response to stress or disease is triggered, these compounds may present in excess and damage tissue, thereby pushing the disease state toward further deterioration. Cytokine overproduction is involved in numerous diseases, such as sepsis, airway and lung injury, renal failure, transplant rejection, skin injuries, intestine injuries, cancer development and metastasis, central nervous system disorders, vaginal bacterial infection, and more.

In certain embodiments, the present invention offers methods for the treatment of disease based upon administration of lipids covalently conjugated through their polar head group to a physiologically acceptable chemical moiety, which may be of high or low molecular weight.

In some embodiments, the lipid compounds (Lipid-conjugates) of the present invention are described by the general formula:

[phosphatidylethanolamine-Y]n-X

[phosphatidylserine-Y]n-X

[phosphatidylcholine-Y]n-X

[phosphatidylinositol-Y]n-X

[phosphatidylglycerol-Y]n-X

[phosphatidic acid-Y]n-X

[lyso-phospholipid-Y]n-X

[diacyl-glycerol-Y]n-X

[monoacyl-glycerol-Y]n-X

[sphingomyelin-Y]n-X

[sphingosine-Y]n-X

[ceramide-Y]n-X wherein
Y is either nothing or a spacer group ranging in length from 2 to 30 atoms; and
X is a physiologically acceptable monomer, dimer, oligomer or polymer; and
n, the number of lipid molecules bound to X, is a number from 1 to 1000.

In one embodiment of this invention, n is a number from 1 to 1000. In another embodiment, n is a number from 1 to 500. In another embodiment, n is a number from 2 to 500. In another embodiment, n is a number from 2 to 1000. In another embodiment, n is a number from 1 to 100. In another embodiment, n is a number from 100 to 300. In another embodiment, n is a number from 300 to 500. In another embodiment, n is a number from 500 to 800.

In one embodiment, the lipid compounds of this invention, known herein as lipid conjugates (Lipid-conjugates) are now disclosed to possess a combination of multiple and potent pharmacological effects in addition to the ability to inhibit the extracellular form of the enzyme phospholipase A2. The set of compounds comprising phosphatidylethanolamine covalently bound to a physiologically acceptable monomer or polymer is referred to herein as the PE-conjugates. Related derivatives, in which either phosphatidylserine, phosphatidylcholine, phosphatidylinositol, phosphatidic acid or phosphatidylglycerol are employed in lieu of phosphatidylethanolamine as the lipid moiety provide equivalent therapeutic results, based upon the biological experiments described below for the Lipid-conjugates and the structural similarities shared by these compounds. Other Lipid-conjugate derivatives relevant to this invention are Lipid-conjugates wherein at least one of the fatty acid groups of the lipid moieties at position C1 or C2 of the glycerol backbone are substituted by a long chain alkyl group attached in either ether or alkyl bonds, rather than ester linkage.

As defined by the structural formulae provided herein for the Lipid-conjugates, these compounds may contain between one to one thousand lipid moieties bound to a single physiologically acceptable polymer molecule.

Administration of the Lipid-conjugates in a diversity of animal and cell models of disease invokes remarkable, and unexpected, cytoprotective effects, which are useful in the treatment of disease. They are able to stabilize biological membranes; inhibit cell proliferation; suppress free radical production; suppress nitric oxide production; reduce cell migration across biological barriers; influence chemokine levels, including MCP-1, ENA-78, Gro α, and CX3C; affect gene transcription and modify the expression of MHC antigens; bind directly to cell membranes and change the water structure at the cell surface; inhibit the uptake of oxidized lipoprotein; prevent airway smooth muscle constriction; suppress neurotransmitter release; reduce expression of tumor necrosis factor-α (TNF-α); modify expression of transcription factors such as NFκB; inhibit extracellular degradative enzymes, including collagenase, heparinase, hyaluronidase, in addition to that of PLA2; and inhibit viral infection of white cells. Thus the Lipid-conjugates provide far-reaching cytoprotective effects to an organism suffering from a disease wherein one or more of the presiding pathophysiological mechanisms of tissue damage entails either oxidation insult giving rise to membrane fragility; hyperproliferation behavior of cells giving rise to stenotic plaque formation in vascular tissue, angiogenesis and benign or malignant cancer disease, or psoriasis; aberrant cell migration giving rise to brain injury or tumor cell metastases; excessive expression of chemokines and cytokines associated with central nervous system (CNS) insult, sepsis, ARDS, or immunological disease; cell membrane damage giving rise to CNS insult, CVS disease, or hemolysis; peroxidation of blood proteins and cell membranes giving rise to atherosclerosis or reperfusion injury; excessive nitric oxide production giving rise to CNS insult, reperfusion injury, and septic shock; interaction with major histocompatability antigens (MHC) associated with autoimmune diseases and alloimmune syndromes, such as transplant rejection.

In certain embodiments of the present invention, the useful pharmacological properties of the lipid or Lipid-conjugates may be applied for clinical use, and disclosed herein as methods for treatment of a disease. The biological basis of these methods may be readily demonstrated by standard cellular and animal models of disease as described below.

While pharmacological activity of the Lipid-conjugates described herein may be due in part to the nature of the lipid moiety, the multiple and diverse combination of pharmacological properties observed for the Lipid-conjugates emerges from the ability of the compound structure to act essentially as several different drugs in one chemical entity. Thus, for example, internal mucosal injury, as may occur in colitis or Crohn's disease, may be attenuated by any one or all of the pharmaceutical activities of immune suppression, anti-inflammation, anti-oxidation, nitric oxide production, or membrane stabilization. Protection of blood vessels from periluminal damage, as may occur in atherosclerosis, may entail activity from anti-proliferative, anti-chemokine, antioxidant, or antimigratory effects. Treatment or prevention of allergic rhinitis or obstructive respiratory disease may involve any one of the many activities of the Lipid-conjugates ranging from suppression of nitric oxide, anti-chemokine, anti-proliferative, or membrane stabilization effects.

The use of a single chemical entity with potent anti-oxidant, membrane-stabilizing, anti-proliferative, anti-chemokine, anti-migratory, and anti-inflammatory activity provides increased cytoprotection relative to the use of several different agents each with a singular activity. The use of a single agent having multiple activities over a combination or plurality of different agents provides uniform delivery of an active molecule, thereby simplifying issues of drug metabolism, toxicity and delivery. The compounds of the present invention also exhibit properties present only in the combined molecule, not in the individual components.

In certain embodiments, the compounds of the invention may be used for acute treatment of temporary conditions, or may be administered chronically, especially in the case of progressive, recurrent, or degenerative disease. In one embodiment of the invention, the concentrations of the compounds will depend on various factors, including the nature of the condition to be treated, the condition of the patient, the route of administration and the individual tolerability of the compositions.

In another embodiment, the invention provides low-molecular weight Lipid-conjugates, previously undisclosed and unknown to possess pharmacological activity, of the general formula:

[Phosphatidylethanolamine-Y]n-X

[Phosphatidylserine-Y]n-X

[Phosphatidylcholine-Y]n-X

[Phosphatidylinositol-Y]n-X

[Phosphatidylglycerol-Y]n-X

[Phosphatidic acid-Y]n-X

[lyso-phospholipid-Y]n-X

[diacyl-glycerol-Y]n-X

[monoacyl-glycerol-Y]n-X

[sphingomyelin-Y]n-X

[sphingosine-Y]n-X

[ceramide-Y]n-X wherein

Y is either nothing or a spacer group ranging in length from 2 to 30 atoms; and

X is salicylate, salicylic acid, aspirin, a monosaccharide, lactobionic acid, maltose, an amino acid, glycine, carboxylic acid, acetic acid, butyric acid, dicarboxylic acid, glutaric acid, succinic acid, fatty acid, dodecanoic acid, didodecanoic acid, bile acid, cholic acid, cholesterylhemmisuccinate, a dipeptide, a disaccharide, a trisaccharide, an oligosaccharide, an oligopeptide, or a di- or trisaccharide monomer unit of heparin, heparan sulfate, keratin, keratan sulfate, chondroitin, chondoitin-6-sulfate, chondroitin-4-sulfate, dermatin, dermatan sulfate, dextran, or hyaluronic acid, a glycosaminoglycan, polygeline ('haemaccel'), alginate, hydroxyethyl starch (hetastarch), polyethylene glycol, polycarboxylated polyethylene glycol, chondroitin-6-sulfate, chondroitin-4-sulfate, keratin, keratin sulfate, heparan sulfate, dermatin, dermatan sulfate, carboxymethylcellulose, heparin, dextran, or hyaluronic acid; and n, the number of lipid molecules bound to X, is a number from 1 to 1000.

In certain embodiments of this invention, n is a number from 1 to 1000. In some embodiments, n is a number from 1 to 500. In other embodiments, n is a number from 1 to 100. In yet other embodiments, n is a number from 100 to 300. In further embodiments, n is a number from 300 to 500. In yet further embodiments, n is a number from 500 to 800.

In certain embodiments of the invention, these Lipid-conjugate derivatives possess wide-spectrum pharmacological activity and, as pharmaceutical agents administered to treat disease, are considered analogous to the Lipid-conjugates comprised from high molecular weight polymers. Other lipid-conjugate derivatives relevant to this invention are glycerolipid moieties in which at least one of the two long chain alkyl groups in position C1 and C2 of the glycerol backbone are attached in ether or alkyl bonds, rather than ester linkage.

The present invention is further illustrated in the following examples of the therapeutic Lipid-conjugate compounds, their chemical preparation, their anti-disease activity, and methods of use as pharmaceutical compositions in the treatment of disease.

Compounds

In the methods, according to embodiments of the invention, the Lipid-conjugates administered to the subject are comprised from at least one lipid moiety covalently bound through an atom of the polar head group to a monomer or polymeric moiety (referred to herein as the conjugated moiety) of either low or high molecular weight. When desired, an optional bridging moiety can be used to link the Lipid-conjugates moiety to the monomer or polymeric moiety. The conjugated moiety may be a low molecular weight carboxylic acid, dicarboxylic acid, fatty acid, dicarboxylic fatty acid, acetyl salicylic acid, cholic acid, cholesterylhemisuccinate, or mono- or di-saccharide, an amino acid or dipeptide, an oligopeptide, a glycoprotein mixture, a di- or trisaccharide monomer unit of a glycosaminoglycan such as a repeating unit of heparin, heparan sulfate, hyaluronic acid, chondrotin-sulfate, dermatan, keratan sulfate, or a higher molecular weight peptide or oligopeptide, a polysaccharide, polyglycan, protein, glycosaminoglycan, or a glycoprotein mixture. From a composition aspect, phospholipid-conjugates of high molecular weight, and associated analogues, are the subject of U.S. Pat. No. 5,064,817, as well as the publications cited herein.

In certain embodiments of the invention, when the conjugated carrier moiety is a polymer, the ratio of lipid moieties covalently bound may range from one to one thousand lipid residues per polymer molecule, depending upon the nature of the polymer and the reaction conditions employed. For example, the relative quantities of the starting materials, or the extent of the reaction time, may be modified in order to obtain Lipid-conjugate products with either high or low ratios of lipid residues per polymer, as desired.

The term "moiety" means a chemical entity otherwise corresponding to a chemical compound, which has a valence satisfied by a covalent bond.

Examples of polymers which can be employed as the conjugated moiety for producing Lipid-conjugates for use in the methods of this invention may be physiologically acceptable polymers, including water-dispersible or -soluble polymers of various molecular weights and diverse chemical types, mainly natural and synthestic polymers, such as glycosaminoglycans, hyaluronic acid, heparin, heparin sulfate, chondrotin sulfate, chondrotin-6-sulfate, chondroitin-4-sulfate, keratin sulfate, dermatin, sulfate, plasma expanders, including polygeline ("Haemaccel", degraded gelatin polypeptide crosslinked via urea bridges, produced by "Behring"), "hydroxyethylstarch" (Htastarch, HES) and extrans, food and drug additives, soluble cellulose derivatives (e.g., methylcellulose, carboxymethylcellulose), polyaminoacids, hydrocarbon polymers (e.g., polyethylene), polystyrenes, polyesters, polyamides, polyethylene oxides (e.g., polyethyleneglycols, polycarboxyethyleneglycol), polyvinnylpyrrolidones, polysaccharides, alginates, assimilable gums (e.g., xanthan gum), peptides, injectable blood proteins (e.g., serum albumin), cyclodextrin, and derivatives thereof.

Examples of monomers, dimers, and oligomers which can be employed as the conjugated moiety for producing Lipid-conjugates for use in the methods of the invention may be mono- or disaccharides, carboxylic acid, dicarboxylic acid, fatty acid, dicarboxylic fatty acid, acetyl salicylic acid, cholic acid, cholesterylhemisuccinate, and di- and trisaccharide unit monomers of glycosaminoglycans including heparin, heparan sulfate, hyaluronic acid, chondrotin, chondroitin-6-sulfate, chondroitin-4-sulfate, dermatin, dermatan sulfate, keratin, keratan sulfate, or dextran.

In some cases, according to embodiments of the invention, the monomer or polymer chosen for preparation of the Lipid-conjugate may in itself have select biological properties. For example, both heparin and hyaluronic acid are materials with known physiological functions. In the present invention, however, the Lipid-conjugates formed from these substances as starting materials display a new and wider set of pharmaceutical activities than would be predicted from administration of either heparin or hyaluronic acid which have not been bound by covalent linkage to a phospholipid. It can be shown, by standard comparative experiments as described below, that phosphatidylethanolamine (PE) linked to carboxymethylcellulose (referred to as CMPE, CMC-Peor CME), to hyaluronic acid (referred to as HYPE, HyPE, and Hyal-PE), to heparin (referred to as HEPPE, HepPE, HePPE, Hepa-PE), to chondroitine sulfate A (referred to as CSAPE, CsaPE, CsAPE), to Polygeline (haemaccel) (referred to HemPE, HEMPE), or to hydroxyethylstarch (referred to as HesPE, HESPE), are far superior in terms of potency and range of useful pharmaceutical activity to the free conjugates (the polymers above and the like). In fact, these latter substances are, in general, not considered useful in methods for treatment of most of the diseases described herein, and for those particular cases wherein their use is medically prescribed, such as ischemic vascular disease, the concentrations for their use as drugs are are several orders of magnitude higher. Thus, the combination of a phospholipid such as phosphatidylethanolamine, or related phospholipids which differ with regard to the polar head group, such as phosphatidylserine (PS), phosphatidylcholine (PC), phosphatidylinositol (PI), and phosphatidylglycerol (PG), results in the formation of a compound which has novel pharmacological properties when compared to the starting materials alone.

The biologically active lipid conjugates described herein can have a wide range of molecular weight, e.g., above 50,000 (up to a few hundred thousands) when it is desirable to retain the Lipid conjugate in the vascular system and below 50,000 when targeting to extravascular systems is desirable. The sole limitation on the molecular weight and the chemical structure of the conjugated moiety is that it does not result in a Lipid-conjugate devoid of the desired biological activity, or lead to chemical or physiological instability to the extent that the Lipid-conjugate is rendered useless as a drug in the method of use described herein.

In one embodiment, a compound according to embodiments of the invention is represented by the structure of the general formula (A):

(A)

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer, wherein X is a glycosaminoglycan; and
n is a number from 1 to 1000;
wherein any bond between L, Z, Y and X is either an amide or an esteric bond.

In certain embodiments, a compound according to embodiments of the invention is represented by the structure of the general formula (I):

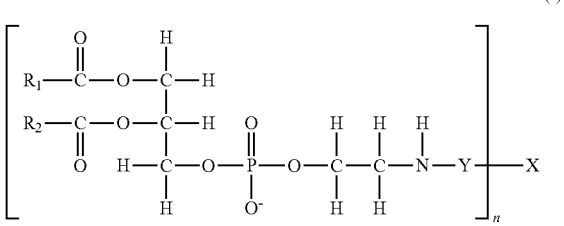

(I)

wherein

R₁ is a linear, saturated, mono-unsaturated, or poly-unsaturated, alkyl chain ranging in length from 2 to 30 carbon atoms;

R₂ is a linear, saturated, mono-unsaturated, or poly-unsaturated, alkyl chain ranging in length from 2 to 30 carbon atoms;

Y is either nothing or a spacer group ranging in length from 2 to 30 atoms; and

X is either a physiologically acceptable monomer, dimer, oligomer or a physiologically acceptable polymer, wherein X is a glycosaminoglycan; and n is a number from 1 to 1,000;

wherein if Y is nothing the phosphatidylethanolamine is directly linked to X via an amide bond and if Y is a spacer, the spacer is directly linked to X via an amide or an esteric bond and to the phosphatidylethanolamine via an amide bond.

Preferred compounds for use in the methods of the invention comprise one of the following as the conjugated moiety X: acetate, butyrate, glutarate, succinate, dodecanoate, didodecanoate, maltose, lactobionic acid, dextran, alginate, aspirin, cholate, cholesterylhemisuccinate, carboxymethylcellulose, heparin, hyaluronic acid, polygeline (haemaccel), polyethyleneglycol, and polycarboxylated polyethylene glycol. The polymers used as starting material to prepare the PE-conjugates may vary in molecular weight from 1 to 2,000 kDa.

Examples of phosphatidylethanolamine (PE) moieties are analogues of the phospholipid in which the chain length of the two fatty acid groups attached to the glycerol backbone of the phospholipid varies from 2-30 carbon atoms length, and in which these fatty acids chains contain saturated and/or unsaturated carbon atoms. In lieu of fatty acid chains, alkyl chains attached directly or via an ether linkage to the glycerol backbone of the phospholipid are included as analogues of PE. According to the present invention, a most preferred PE moiety is dipalmitoylphosphatidy-ethanolamine.

Phosphatidyl-ethanolamine and its analogues may be from various sources, including natural, synthetic, and semisynthetic derivatives and their isomers.

Phospholipids which can be employed in lieu of the PE moiety are N-methyl-PE derivatives and their analogues, linked through the amino group of the N-methyl-PE by a covalent bond; N,N-dimethyl-PE derivatives and their analogues linked through the amino group of the N,N-dimethyl-PE by a covalent bond, phosphatidylserine (PS) and its analogues, such as palmitoyl-stearoyl-PS, natural PS from various sources, semisynthetic PSs, synthetic, natural and artifactual PSs and their isomers. Other phospholipids useful as conjugated moieties in embodiments of this invention are phosphatidylcholine (PC), phosphatidylinositol (PI), phosphatidic acid and phosphoatidylglycerol (PG), as well as derivatives thereof comprising either phospholipids, lysophospholipids, phosphatidyic acid, sphingomyelins, lysosphingomyelins, ceramide, and sphingosine.

For PE-conjugates and PS-conjugates, the phospholipid is linked to the conjugated monomer or polymer moiety through the nitrogen atom of the phospholipid polar head group, either directly or via a spacer group. For PC, PI, and PG conjugates, the phospholipid is linked to the conjugated monomer or polymer moiety through either the nitrogen or one of the oxygen atoms of the polar head group, either directly or via a spacer group.

In other embodiments, a compound according to embodiments of the invention is represented by the structure of the general formula (II):

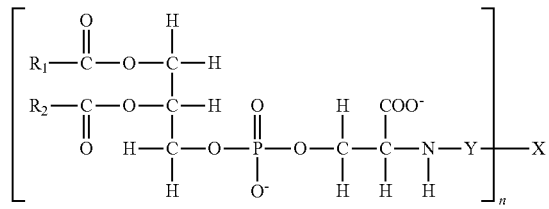

wherein

R₁ is a linear, saturated, mono-unsaturated, or poly-unsaturated, alkyl chain ranging in length from 2 to 30 carbon atoms;

R₂ is a linear, saturated, mono-unsaturated, or poly-unsaturated, alkyl chain ranging in length from 2 to 30 carbon atoms;

Y is either nothing or a spacer group ranging in length from 2 to 30 atoms;

X is a physiologically acceptable monomer, dimer, oligomer or polymer wherein x is a glycosaminoglycan; and n is a number from 1 to 1000;

wherein if Y is nothing the phosphatidylserine is directly linked to X via an amide bond and if Y is a spacer, the spacer is directly linked to X via an amide or an esteric bond and to the phosphatidylserine via an amide bond.

In certain embodiments, the compound according to the invention be [phosphatidylserine-Y]n-X, wherein Y is either nothing or a spacer group ranging in length from 2 to 30 atoms, X is a physiologically acceptable monomer, dimer, oligomer or polymer wherein x is a glycosaminoglycan, and n is a number from 1 to 1000, wherein the phosphatidylserine may be bonded to Y or to X, if Y is nothing, via the COO⁻ moiety of the phosphatidylserine.

In further embodiments, a compound according to embodiments of the invention is represented by the structure of the general formula (III):

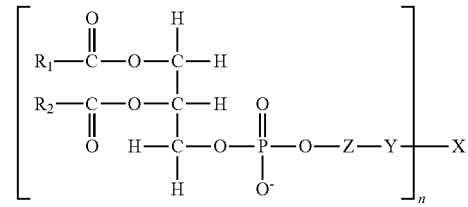

wherein

R₁ is a linear, saturated, mono-unsaturated, or poly-unsaturated, alkyl chain ranging in length from 2 to 30 carbon atoms;

R₂ is a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a physiologically acceptable monomer, dimer, oligomer, or polymer, wherein x is a glycosaminoglycan; and n is a number from 1 to 1000;

wherein any bond between the phosphatidyl, Z, Y and X is either an amide or anesteric bond.

In yet other embodiments, a compound according to embodiments of the invention is represented by the structure of the general formula (IV)

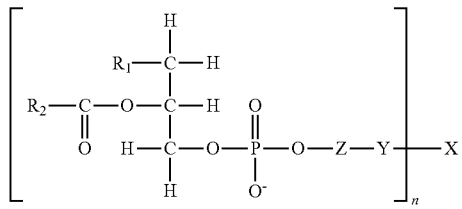

(IV)

wherein
$R_1$ is either hydrogen or a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Z is either nothing, inositol, choline, or glycerol;
Y is either nothing or a spacer group ranging in length from 2 to 30 atoms;
X is a physiologically acceptable monomer, dimer, oligomer, or polymer, wherein x is a glycosaminoglycan; and
n is a number from 1 to 1000;
wherein any bond between the phospholipid, Z, Y and X is either an amide or an esteric bond.

In certain embodiments, a compound according to embodiments of the invention is represented by the structure of the general formula (V):

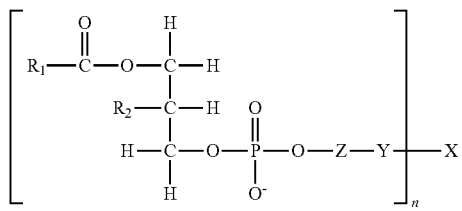

(V)

wherein
$R_1$ is a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, inositol, choline, or glycerol;
Y is either nothing or a spacer group ranging in length from 2 to 30 atoms;
X is a physiologically acceptable monomer, dimer, oligomer, or polymer, wherein x is a glycosaminoglycan; and
n is a number from 1 to 1000;
wherein any bond between the phospholipid, Z, Y and X is either an amide or an esteric bond.

In some embodiments, a compound according to embodiments of the invention is represented by the structure of the general formula (VI):

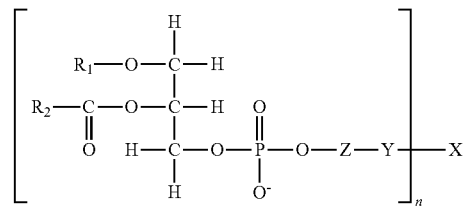

(VI)

wherein
$R_1$ is either hydrogen or a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Z is either nothing, inositol, choline, or glycerol;
Y is either nothing or a spacer group ranging in length from 2 to 30 atoms;
X is a physiologically acceptable monomer, dimer, oligomer, or polymer, wherein x is a glycosaminoglycan; and
n is a number from 1 to 1000;
wherein any bond between the phospholipid, Z, Y and X is either an amide or an esteric bond.

In other embodiments, a compound according to embodiments of the invention is represented by the structure of the general formula (VII):

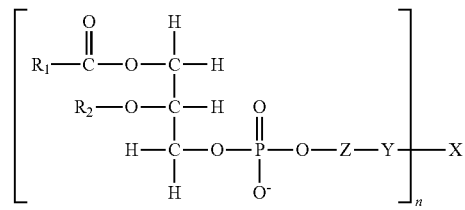

(VII)

wherein
$R_1$ is a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, inositol, choline, or glycerol;
Y is either nothing or a spacer group ranging in length from 2 to 30 atoms;
X is a physiologically acceptable monomer, dimer, oligomer, or polymer, wherein x is a glycosaminoglycan; and
n is a number from 1 to 1000;
wherein any bond between the phospholipid, Z, Y and X is either an amide or an esteric bond.

In some embodiments of the invention, phosphatidylcholine (PC), Phosphatidylinositol (PI), phosphatidic acid (PA), wherein Z is nothing, and Phosphatidylglycerol (PG) conjugates are herein defined as compounds of the general formula (III).

In certain embodiments of the invention Y is nothing. Non limiting examples of suitable divalent groups forming the optional bridging group (spacer) Y, according to embodiments of the invention, are straight or branched chain alkylene, e.g., of 2 or more, preferably 4 to 30 carbon atoms, —CO-alkylene-CO, —NH-alkylene-NH—, —CO-alkylene- NH—, —NH-alkylene-NHCO-alkylene-NH—, an amino acid, cycloalkylene, wherein alkylene in each instance, is straight or branched chain and contains 2 or more, preferably 2 to 30 atoms in the chain, —(—O—CH(CH$_3$)CH$_2$—)$_x$— wherein x is an integer of 1 or more.

According to embodiments of the invention, in addition to the traditional phospholipid structure, related derivatives for use in this invention are phospholipids modified at the C1 or C2 position to contain an ether or alkyl bond instead of an ester bond. In some embodiments of the invention, the alkyl phospholipid derivatives and ether phospholipid derivatives are exemplified herein.

In still other embodiments, a compound according to embodiments of the invention is represented by the structure of the general formula (VIII):

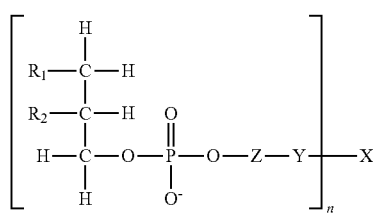

(VIII)

wherein
R$_1$ is a linear, saturated, mono-unsaturated, or poly-unsaturated, alkyl chain ranging in length from 2 to 30 carbon atoms;
R$_2$ is either hydrogen or a linear, saturated, mono-unsaturated, or poly-unsaturated, alkyl chain ranging in length from 2 to 30 carbon atoms;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer, wherein x is a glycosaminoglycan; and
n is a number from 1 to 1000;
wherein any bond between the phospholipid, Z, Y and X is either an amide or an esteric bond.

In still further embodiments, a compound according to embodiments of the invention is represented by the structure of the general formula (IX):

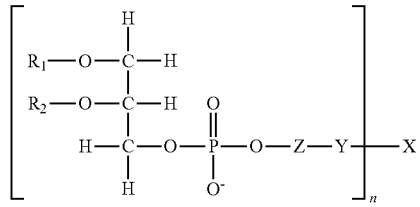

(IX)

wherein
R$_1$ is either hydrogen or a linear, saturated, mono-unsaturated, or poly-unsaturated, alkyl chain ranging in length from 2 to 30 carbon atoms;
R$_2$ is either hydrogen or a linear, saturated, mono-unsaturated, or poly-unsaturated, alkyl chain ranging in length from 2 to 30 carbon atoms;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer, wherein x is a glycosaminoglycan; and
n is a number from 1 to 1000;
wherein any bond between the phospholipid, Z, Y and X is either an amide or an esteric bond.

In certain embodiments, a compound according to embodiments of the invention is represented by the structure of the general formula (IXa):

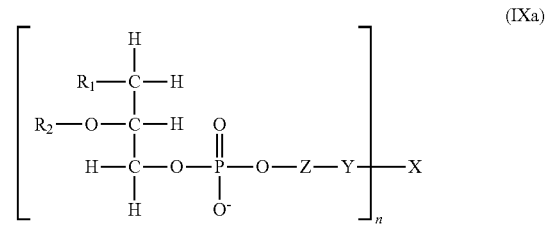

(IXa)

wherein
R$_1$ is either hydrogen or a linear, saturated, mono-unsaturated, or poly-unsaturated, alkyl chain ranging in length from 2 to 30 carbon atoms;
R$_2$ is either hydrogen or a linear, saturated, mono-unsaturated, or poly-unsaturated, alkyl chain ranging in length from 2 to 30 carbon atoms;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer, wherein x is a glycosaminoglycan; and
n is a number from 1 to 1000;
wherein any bond between the phospholipid, Z, Y and X is either an amide or an esteric bond.

In certain other embodiments, the a compound according to embodiments of the invention is represented by the structure of the general formula (IXb):

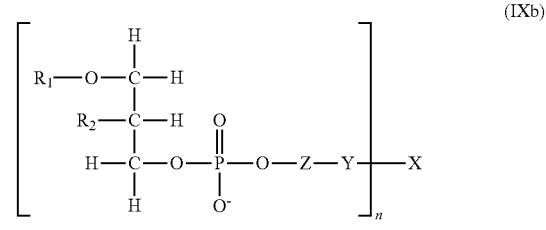

(IXb)

wherein
R$_1$ is either hydrogen or a linear, saturated, mono-unsaturated, or poly-unsaturated, alkyl chain ranging in length from 2 to 30 carbon atoms;
R$_2$ is either hydrogen or a linear, saturated, mono-unsaturated, or poly-unsaturated, alkyl chain ranging in length from 2 to 30 carbon atoms;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer, wherein x is a glycosaminoglycan; and
n is a number from 1 to 1000;

wherein any bond between the phospholipid, Z, Y and X is either an amide or an esteric bond.

In further embodiments, a compound according to embodiments of the invention is represented by the structure of the general formula (X):

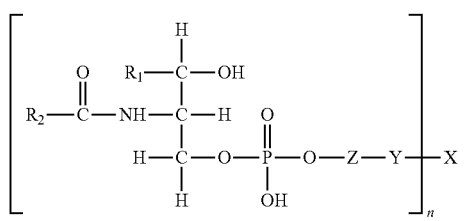

(X)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a physiologically acceptable monomer, dimer, oligomer, or polymer, wherein x is a glycosaminoglycan; and n is a number from 1 to 1000;

wherein any bond between the ceramide phosphoryl, Z, Y and X is either an amide or an esteric bond.

In still further embodiments, a compound according to embodiments of the invention is represented by the structure of the general formula (XI):

$$\left[ \begin{array}{c} H \\ R_1-C-OH \\ H-C-NH-Y \\ HO-C-H \\ H \end{array} \right]_n X$$

(XI)

wherein $R_1$ is a linear, saturated, mono-unsaturated, or poly-unsaturated, alkyl chain ranging in length from 2 to 30 carbon atoms;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein if Y is nothing the sphingosyl is directly linked to X via an amide bond and if Y is a spacer, the spacer is directly linked to X and to the sphingosyl via an amide bond and to X via an amide or an esteric bond.

In yet further embodiments, a compound according to embodiments of the invention is represented by the structure of the general formula (XII):

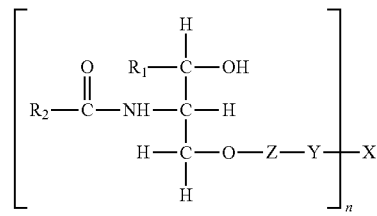

(XII)

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

L is ceramide;

Z is either nothing, ethanolamine, serine, inositol, choline, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the ceramide, Z, Y and X is either an amide or an esteric bond.

In some embodiments, a compound according to embodiments of the invention is represented by the structure of the general formula (XIII):

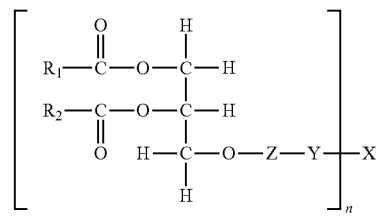

(XIII)

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the diglyceryl, Z, Y and X is either an amide or an esteric bond.

In certain embodiments, a compound according to embodiments of the invention is represented by the structure of the general formula (XIV):

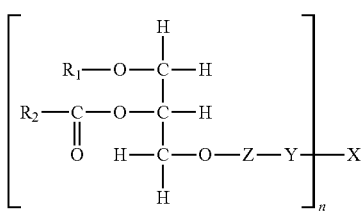

(XIV)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the glycerolipid, Z, Y and X is either an amide or an esteric bond.

In additional embodiments, a compound according to embodiments of the invention is represented by the structure of the general formula (XV):

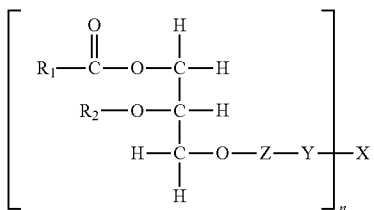

(XV)

wherein $R_1$ is a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the glycerolipid, Z, Y and X is either an amide or an esteric bond.

In other embodiments, a compound according to embodiments of the invention is represented by the structure of the general formula (XVI):

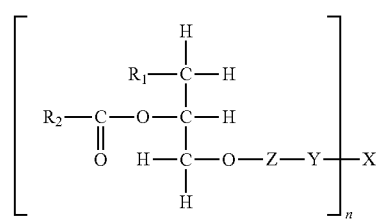

(XVI)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the lipid, Z, Y and X is either an amide or an esteric bond.

In yet other embodiments, a compound according to embodiments of the invention is represented by the structure of the general formula (XVII):

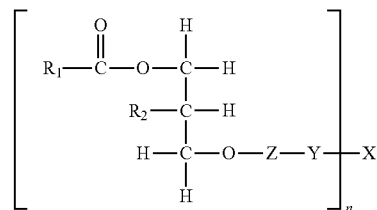

(XVII)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the lipid, Z, Y and X is either an amide or an esteric bond.

In still other embodiments, a compound according to embodiments of the invention is represented by the structure of the general formula (XVIII):

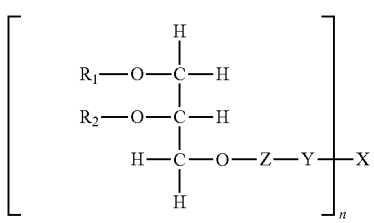

(XVIII)

wherein
$R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the lipid, Z, Y and X is either an amide or an esteric bond.

In further embodiments, a compound according to embodiments of the invention is represented by the structure of the general formula (XIX):

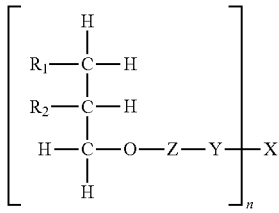

(XIX)

wherein
$R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the lipid, Z, Y and X is either an amide or an esteric bond.

In yet further embodiments, a compound according to embodiments of the invention is represented by the structure of the general formula (XX):

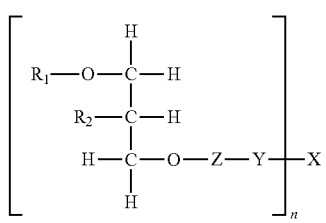

(XX)

wherein
$R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the lipid, Z, Y and X is either an amide or an esteric bond.

In yet still further embodiments, a compound according to embodiments of the invention is represented by the structure of the general formula (XXI):

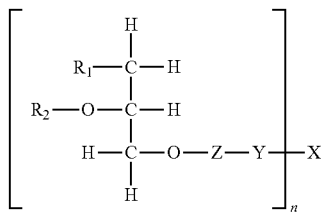

(XIX)

wherein
$R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the lipid, Z, Y and X is either an amide or an esteric bond.

In certain embodiments of the invention, the glycosaminoglycan may be, inter alia, hyaluronic acid, heparin, heparan sulfate, chondrotin sulfate, keratin, keratan sulfate, dermatan sulfate or a derivative thereof.

In some embodiments, the glycosaminoglycan is di- and trisaccharide unit monomers of glycosaminoglycans. In certain embodiments, the chondroitin sulfate may be, inter alia, chondroitin-6-sulfate, chondroitin-4-sulfate or a derivative thereof.

In certain embodiments of the invention, the sugar rings of the glycosaminoglycan are intact. In some embodiments, intact refers to closed. In other embodiments, intact refers to natural. In yet other embodiments, intact refers to unbroken.

In certain embodiments of the invention, the structure of the lipid or phospholipids in any compound according to the invention is intact. In some embodiments, the natural structure of the lipid or phospholipids in any compound according to the invention is maintained.

In some embodiments, the compounds according to the invention are biodegradable.

In certain embodiments, the compound according to the invention is a compound represented by the structure of the general formula (A):

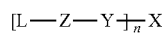

(A)

wherein
L is phosphatidyl;
Z is ethanolamine, wherein L and Z are chemically bonded resulting in phosphatidylethanolamine;
Y is nothing;
X is hyaluronic acid; and
n is a number from 1 to 1000;
wherein any bond between the phosphatidylethanolamine and the hyaluronic acid is an amide bond.

In some embodiments, the compound according to the invention is a compound represented by the structure of the general formula (A):

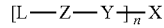

(A)

wherein
L is phosphatidyl;
Z is ethanolamine, wherein L and Z are chemically bonded resulting in phosphatidylethanolamine;
Y is nothing;
X is chondroitin sulfate; and
n is a number from 1 to 1000;
wherein any bond between the phosphatidylethanolamine and the chondroitin sulfate is an amide bond.

In certain embodiments, the invention provides methods of treating a subject suffering from asthma, comprising the step of administering to a subject any one of the compounds according to the invention, or any combination thereof, in an amount effective to treat the subject suffering from asthma. In some of these embodiments, the compounds according to the invention include, inter alia, the compounds represented by the structures of the general formulae: (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII) or any combination thereof. In other embodiments, the invention provides methods of preventing asthma in a subject.

In certain embodiments, the invention provides methods of treating a subject suffering from rhinitis, comprising the step of administering to a subject any one of the compounds according to the invention, or any combination thereof, in an amount effective to treat the subject suffering from rhinitis. In some of these embodiments, the compounds according to the invention include, inter alia, the compounds represented by the structures of the general formulae: (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII) or any combination thereof. In other embodiments, the invention provides methods of preventing rhinitis in a subject.

In certain embodiments, the invention provides methods of treating a subject suffering from allergic rhinitis, comprising the step of administering to a subject any one of the compounds according to the invention, or any combination thereof, in an amount effective to treat the subject suffering from allergic rhinitis. In some of these embodiments, the compounds according to the invention include, inter alia, the compounds represented by the structures of the general formulae: (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII) or any combination thereof. In other embodiments, the invention provides methods of preventing allergic rhinitis in a subject.

In certain embodiments, the invention provides methods of treating a subject suffering from chronic obstructive pulmonary disease, comprising the step of administering to a subject any one of the compounds according to the invention, or any combination thereof, in an amount effective to treat the subject suffering from chronic obstructive pulmonary disease. In some of these embodiments, the compounds according to the invention include, inter alia, the compounds represented by the structures of the general formulae: (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII) or any combination thereof. In other embodiments, the invention provides methods of preventing chronic obstructive pulmonary disease in a subject.

In certain embodiments, the invention provides methods of treating a subject suffering from an obstructive respiratory disease, comprising the step of administering to a subject any one of the compounds according to the invention, or any combination thereof, in an amount effective to treat the subject suffering from an obstructive respiratory disease. In another embodiment, the compounds according to the invention include, inter alia, the compounds represented by the structures of the general formulae: (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII) or any combination thereof. In some embodiments, the obstructive respiratory disease is asthma. In some embodiments, the obstructive respiratory disease is rhinitis. In some embodiments, the obstructive respiratory disease is allergic rhinitis. In some embodiments, the obstructive respiratory disease is chronic obstructive pulmonary disease. In some embodiments, the invention provides methods of preventing asthma, rhinitis, allergic rhinitis, chronic obstructive pulmonary disease, obstructive respiratory disease, or a combination thereof, in a subject.

Illustrative of preferred Lipid-conjugates for use in the methods according to embodiments of this invention are those in which the lipid/phospholipid moiety is linked directly or indirectly through a bridging moiety listed below.

| phospholipid | spacer | polymer (m.w.) | abbreviation |
| --- | --- | --- | --- |
| PE | Dicarboxylic acid + Diamine | Polygeline (haemaccel) (4-40 kDa) | HeMPE; HemPE |
| PE | None | Carboxymethylcellulose (20-500 kDa) | CMPE; CMC-PE |

-continued

| phospholipid | spacer | polymer (m.w.) | abbreviation |
|---|---|---|---|
| PE | None | Hyaluronic acid (2-2000 kDa) | HYPE (HyPE) |
| PE | Dipalmitoic acid | Hyaluronic acid (2-2000 kDa) | HYPE-dipalmitoyl |
| PE | None | Polyethylene glycol | |
| PE | Y | Hydroxyethylstarch | HESPE; HesPE |
| PE | Dicarboxylic acid + Diamine | Dextran (1-2,000 kDa) | DexPE |
| PE | None | Dextran (1-2,000 kDa) | DexPE |
| PE | None | Albumin | |
| PE | None | Alginate (2-2000 kDa) | |
| PE | None | Polyamino acid | |
| PE | None | Lactobionic acid | |
| PE | None | Acetylsalicylate | |
| PE | None | Cholesteryl-hemmisuccinate | |
| PE | None | Maltose | |
| PE | Y | None | Cholic acid |
| PE | None | Polycarboxylated polyethylene glycol | |
| PE | None | Heparin (0.5-110 kDa) | HEPPE; HEPE; HepPE |
| Dimyristoyl-PE | Y | Variable | DMPE |
| Dimyristoyl-PE | Y | Hyaluronic acid | HyDMPE |
| PS | Y | Polygeline (haemaccel) | |
| PS | Y | Heparin | |
| PS | Y | Hyaluronic acid | |
| PC | Y | Polygeline (haemaccel) | |
| PC | Y | Heparin | |
| PC | Y | Hyaluronic acid | |
| PI | Y | Polygeline (haemaccel) | |
| PI | Y | Heparin | |
| PI | Y | Hyaluronic acid | |
| PG | Y | Polygeline (haemaccel) | |
| PG | Y | Heparin | |
| PE | Y | Chondoitin sulfates | CSPE |
| PE | Y | Polygeline (haemaccel) | |
| PG | Y | Hyaluronic acid | |

In some embodiments of the invention, the compounds administered are HyPE, CSAPE, CMPE, HemPE, HesPE, DexPE and As-PE and pharmaceutically acceptable salts thereof, in combination with a physiologically acceptable carrier or solvent. These polymers, when chosen as the conjugated moiety, may vary in molecular weights from 200 to 2,000,000 Daltons. Various molecular weight species have been shown to have the desired biological efficacy, as shown in the section below.

In addition to the compounds of the Examples, further illustrative compounds of this invention are set forth in the section below.

Novel Compounds

Low molecular weight Lipid-conjugates, in which the conjugated moiety (X) is a monomer such as a salicylate, a bile acid, or cholesterylhemmisuccinate, or a di- or trisaccaharide unit monomer of a polyglycosoaminoglycan such as heparin, heparan sulfate, chondrotin-6-sulfate, chondroitin-4-sulfate, hyaluronic acid, keratin, keratan sulfate, dermatin, or dermatan sulfate, have not been described before. According to embodiments of the invention, these new compounds display a similar biological activity profile as demonstrated below for the other Lipid-conjugates and have the general formula

[Phosphatidylethanolamine-Y]$_n$—X

[Phosphatidylserine-Y]$_n$—X

[Phosphatidylcholine-Y]$_n$—X

[Phosphatidylinositol-Y]$_n$—X

[Phosphatidylglycerol-Y]$_n$—X

[Phosphatidic acid-Y]$_n$—X

[lyso-phospholipid-Y]$_n$—X

[diacyl-glycerol-Y]$_n$—X

[monoacyl-glycerol-Y]$_n$—X

[sphingomyelin-Y]$_n$—X

[sphingosine-Y]$_n$—X

[ceramide-Y]$_n$—X wherein
Y is either nothing or a spacer group ranging in length from 2 to 30 atoms;
X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisacharide, or a di- or trisaccharide monomer unit of heparin, heparan sulfate, keratin, keratan sulfate, chondroitin, chondoitin-6-sulfate, chondroitin-4-sulfate, dermatin, dermatan sulfate, dextran, hyaluronic acid or glycosaminoglycan; and n is the number of lipid moiety molecules bound to a molecule of X wherein n is a number from 1 to 100.

In certain embodiments, the glycosaminoglycan is a polymer (X) of disaccharide units. In some embodiments, the number of the disaccharide units in the polymer is m. In other embodiments, m is a number from 2-10,000. In yet other embodiments, m is a number from 2-500. In still other embodiments, m is a number from 2-1000. In yet still other embodiments, m is a number from 50-500. In some embodiments, m is a number from 2-2000. In some other embodiments, m is a number from 500-2000. In further embodiments, m is a number from 1000-2000. In still further embodiments, m is a number from 2000-5000. In yet further embodiments, m is a number from 3000-7000. In yet still further embodiments, m is a number from 5000-10,000. In some embodiments, a disaccharide unit of a glycosaminoglycan may be bound to one lipid or phospholipid moiety. In certain embodiments, each disaccharide unit of the glycosaminoglycan may be bound to zero or one lipid or phospholipid moieties. In some embodiments, the lipid or phospholipid moieties are bound to the —COOH group of the disaccharide unit. In other embodiments, the bond between the lipid or phospholipid moiety and the disaccharide unit is an amide bond.

According to certain embodiments, this invention provides lipid-GAG conjugate or phospholipid-GAG conjugate of this invention, and methods of use thereof, wherein said conjugate represented by the structures of the general formulae (A), (I), (II), (III), (IV), (V), (VI), (VII), (VIII), (IX), (IXa), (IXb), (X), (Xa), (XI), (XII), (XIIa), (XIII), (XIV), (XV), (XVI), (XVII), (XVIII), (XIX), (XX), (XXI), and (XXII). In some embodiments, the average molecular weight of said GAG is between 5 kD to 90 kD. In some embodiments, the average molecular weight of said GAG is between 5 kD to 60 kD. In some embodiments, the average molecular weight of said GAG is between 5 kD to 40 kD. In some embodiments, the average molecular weight of said GAG is between 5 kD to 15 kD. In some embodiments, the average molecular weight of said GAG is between 5 kD to 20 kD. In some embodiments, the lipid-GAG conjugate is a phospholipid-GAG conjugate In certain embodiments of this invention, low molecular weight phosphatidylethanolamine (PE)-conjugates are defined hereinabove as the compounds of formula (I) wherein:

$R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms;

X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisaccharide, or a di- or trisaccharide monomer unit of heparin, heparan sulfate, keratin, keratan sulfate, chondroitin, chondoitin-6-sulfate, chondroitin-4-sulfate, dermatin, dermatan sulfate, dextran, hyaluronic acid or glycosaminoglycan; and n is the number of lipid moiety molecules bound to a molecule of X wherein n is a number from 1 to 1000.

In some embodiments, the molecular weight of said glycosaminoglycan is between 5 kD and 20 kD. In other embodiments, n is a number between 1 to 100. In yet other embodiments, said glycosaminoglycan is between 5 kD and 20 kD and n is between 1 to 100.

In certain embodiments of this invention, low molecular weight phosphatidylserine (PS)-conjugates are defined hereinabove as the compounds of formula (II) wherein:

$R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms;

X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisaccharide, or a di- or trisaccharide monomer unit of heparin, heparan sulfate, keratin, keratan sulfate, chondroitin, chondoitin-6-sulfate, chondroitin-4-sulfate, dermatin, dermatan sulfate, dextran, hyaluronic acid or glycosaminoglycan; and n is the number of lipid moiety molecules bound to a molecule of X wherein n is a number from 1 to 1000.

In some embodiments, the molecular weight of said glycosaminoglycan is between 5 kD and 20 kD. In other embodiments, n is a number between 1 to 100. In yet other embodiments, said glycosaminoglycan is between 5 kD and 20 kD and n is between 1 to 100.

In certain embodiments of this invention, Phosphatidylcholine (PC), Phosphatidylinositol (PI), and Phosphatidylglycerol (PG) conjugates are hereinabove defined as the compounds of formula (III) wherein:

$R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisaccharide, or a di- or trisaccharide monomer unit of heparin, heparan sulfate, keratin, keratan sulfate, chondroitin, chondoitin-6-sulfate, chondroitin-4-sulfate, dermatin, dermatan sulfate, dextran, hyaluronic acid or glycosaminoglycan; and n is the number of lipid moiety molecules bound to a molecule of X wherein n is a number from 1 to 1000.

In some embodiments, the molecular weight of said glycosaminoglycan is between 5 kD and 20 kD. In other embodiments, n is a number between 1 to 100. In yet other embodiments, said glycosaminoglycan is between 5 kD and 20 kD and n is between 1 to 100.

Examples of suitable divalent groups forming the optional bridging group Y are straight- or branched-chain alkylene, e.g., of 2 or more, preferably 4 to 18 carbon atoms, —CO-alkylene-CO, —NH-alkylene-NH—, —CO-alkylene-NH—, cycloalkylene, wherein alkylene in each instance, is straight or branched chain and contains 2 or more, preferably 2 to 18 carbon atoms in the chain, —(—O—CH(CH$_3$)CH$_2$—)$_x$— wherein x is an integer of 1 or more.

In some embodiments, in addition to the traditional phospholipid structure, related derivatives for use in this invention are phospholipids modified at the C1 or C2 position to contain an ether or alkyl bond instead of an ester bond. These derivatives are exemplified hereinabove by the general formulae (VIII) and (IX) wherein:
- R$_1$ is a linear, saturated, mono-unsaturated, or poly-unsaturated, alkyl chain ranging in length from 2 to 30 carbon atoms;
- R$_2$ is a linear, saturated, mono-unsaturated, or poly-unsaturated, alkyl chain ranging in length from 2 to 30 carbon atoms;
- Z is either nothing, ethanolamine, serine, inositol, choline, or glycerol;
- Y is either nothing or a spacer group ranging in length from 2 to 30 atoms;
- X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisaccharide, or a di- or trisaccharide monomer unit of heparin, heparan sulfate, keratin, keratan sulfate, chondroitin, chondoitin-6-sulfate, chondroitin-4-sulfate, dermatin, dermatan sulfate, dextran, hyaluronic acid or glycosaminoglycan; and
- n is the number of lipid moiety molecules bound to a molecule of X wherein n is a number from 1 to 1000.

In some embodiments, the molecular weight of said glycosaminoglycan is between 5 kD and 20 kD. In other embodiments, n is a number between 1 to 100. In yet other embodiments, said glycosaminoglycan is between 5 kD and 20 kD and n is between 1 to 100.

In some embodiments, related low molecular weight derivatives for use in this invention are exemplified hereinabove by the general formulae (X), (XI) and (XII) wherein:
- R$_1$ is a linear, saturated, mono-unsaturated, or poly-unsaturated, alkyl chain ranging in length from 2 to 30 carbon atoms;
- R$_2$ is a linear, saturated, mono-unsaturated, or poly-unsaturated, alkyl chain ranging in length from 2 to 30 carbon atoms;
- Z is either nothing, ethanolamine, serine, inositol, choline, or glycerol;
- Y is either nothing or a spacer group ranging in length from 2 to 30 atoms;
- X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisaccharide, or a di- or trisaccharide monomer unit of heparin, heparan sulfate, keratin, keratan sulfate, chondroitin, chondoitin-6-sulfate, chondroitin-4-sulfate, dermatin, dermatan sulfate, dextran, hyaluronic acid or glycosaminoglycan; and
- n is the number of lipid moiety molecules bound to a molecule of X wherein n is a number from 1 to 1000.

In some embodiments, the molecular weight of said glycosaminoglycan is between 5 kD and 20 kD. In other embodiments, n is a number between 1 to 100. In yet other embodiments, said glycosaminoglycan is between 5 kD and 20 kD and n is between 1 to 100.

In some embodiments, related low molecular weight derivatives for use in this invention are exemplified hereinabove by the general formulae (XIII) wherein:
- R$_1$ is a linear, saturated, mono-unsaturated, or poly-unsaturated, alkyl chain ranging in length from 2 to 30 carbon atoms;
- R$_2$ is a linear, saturated, mono-unsaturated, or poly-unsaturated, alkyl chain ranging in length from 2 to 30 carbon atoms;
- Z is either nothing, choline, phosphate, inositol, or glycerol;
- Y is either nothing or a spacer group ranging in length from 2 to 30 atoms;
- X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisaccharide, or a di- or trisaccharide monomer unit of heparin, heparan sulfate, keratin, keratan sulfate, chondroitin, chondoitin-6-sulfate, chondroitin-4-sulfate, dermatin, dermatan sulfate, dextran, hyaluronic acid or glycosaminoglycan; and
- n is the number of lipid moiety molecules bound to a molecule of X wherein n is a number from 1 to 1000.

In some embodiments, the molecular weight of said glycosaminoglycan is between 5 kD and 20 kD. In other embodiments, n is a number between 1 to 100. In yet other embodiments, said glycosaminoglycan is between 5 kD and 20 kD and n is between 1 to 100.

In certain embodiments, related low molecular weight derivatives according to the invention may be exemplified herein by any of the general formulae (A), (I)-(XXI) wherein:

In certain embodiments of the invention, X is covalently conjugated to a lipid. In some embodiments, x is covalently conjugated to a lipid via an amide bond. In other embodiments, x is covalently conjugated to a lipid via an esteric bond. In some embodiments, the lipid is phosphatidylethanolamine. In some embodiments, the GAG may be, inter alia, chondroitin sulfate. In certain embodiments, the conjugate is biodegradable. In some embodiments, the glycosaminoglycan is between 5 kD and 20 kD.

In some embodiments, the invention provides glycosaminoglycans (GAG) compound covalently conjugated to a lipid to obtain a compound having preferred therapeutic properties. In some embodiments, the GAG compound is covalently conjugated to a lipid via an amide bond. In some embodiments, the GAG compound is covalently conjugated to a lipid via an esteric bond. In some embodiments, the lipid may be, inter alia, phosphatidylethanolamine. In some embodiments, the GAG may be, inter alia, chondroitin sulfate. In some embodiments, the conjugate is biodegradable. In some embodiments, the glycosaminoglycan is between 5 kD and 20 kD.

In certain embodiments, this invention is directed to low molecular weight lipid-polymer conjugate comprising a GAG wherein the average molecular weight of said GAG is between 5 kd to 90 kd. In some embodiments, the average molecular weight of said GAG is between 5 kD to 60 kD. In some embodiments, the average molecular weight of said GAG is between 5 kD to 40 kD. In some embodiments, the average molecular weight of said GAG is between 5 kD to 15 kD. In some embodiments, the average molecular weight of said GAG is between 5 kD to 20 kD. In some embodiments, the average molecular weight of said GAG is between 5 kD to 25 kD.

Cell surface GAG play a key role in protecting cells from diverse damaging agents and processes, such as reactive oxygen species and free radicals, endotoxins, cytokines, invasion promoting enzymes, and agents that induce and/or facilitate degradation of extracellular matrix and basal membrane, cell invasiveness, white cell extravasation and infiltration, chemotaxis, and others. In addition, cell surface GAG protect cells from bacterial, viral and parasite infection, and their stripping exposes the cell to interaction and subsequent internalization of the microorganism. Enrichment of cell surface GAG would thus assist in protection of the cell from injurious processes. Thus, in some embodiments of the invention, PLA2 inhibitos were conjugated to GAGs or GAG-mimicking molecules. In other embodiments, these Lipid-conjugates, provides wide-range protection from diverse injurious processes, and are effective in amelioration of diseases that requires cell protection from injurous biochemical medistors.

In certain embodiments, GAG-mimicking molecule may be, inter alia, a negatively charged molecule. In some embodiments, GAG-mimicking molecule may be, inter alia, a salicilate derivative. In some embodiments, GAG-mimicking molecule may be, inter alia, a dicarboxylic acid.

Preparation of Compounds

The preparation of some high molecular weight Lipid-conjugates is the subject of U.S. Pat. No. 5,064,817, which is incorporated herein by reference. These synthetic methods are reiterated below and are considered to be applicable as well to the preparation of low molecular, i.e. Lipid-conjugates comprising monomers and dimers as the conjugated moiety, with modifications in the procedure as readily evident to one skilled in the art.

When the starting compound chosen for the conjugated moiety has a substituent which is or can be rendered reactive to a substituent on the starting Lipid compound, the conjugated carrier moiety may be linked directly to lipid molecule(s) to produce the a Lipid-conjugate. When it does not, a bifunctional linking starting material can be used to link the two molecules indirectly.

Lipid-conjugates are prepared by linking a polar conjugate, e.g., a monomer or polymer, directly or indirectly to a PL moiety according to the general reaction schemes delineated in U.S. Pat. No. 5,064,817 and according to US Publication 2011-0130555.

For example, with acylated PE used as precursor for the PE conjugate, various lengths of dicarboxylic acids can be used as spacers. These acids can be linked to natural, semi-synthetic or synthetic PE.

For example, PE can be linked to aminodextran indirectly as delineated in U.S. Pat. No. 5,064,817 and US Publication 2011-0130555.

Polymers with carboxylic groups, such as polyamino acids, carboxymethyl cellulose or polymers to which fatty acids have been linked, can be linked directly to PE according to the scheme delineated in U.S. Pat. No. 5,064,817.

It is to be understood that these examples are given by way of illustration only and are not to be construed as limiting the invention either in spirit of in scope, as many modifications both in reagents and methods could be possible to those skilled in the art. Based on the wide spectrum of pharmacological properties exhibited by Lipid-conjugates, it is likely that compounds covered by Formula I-XXI, in addition to those explicitly described above, have the same valuable biological activities demonstrate to be useful in the methods of treating disease described below.

In certain embodiments, the invention provides processes for the preparation of a compound represented by the structure of the general formula (A):

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer, wherein X is a glycosaminoglycan; and
n is a number from 1 to 1000;
wherein any bond between L, Z, Y and X is either an amide or an esteric bond,
including, inter alia, the steps of:
conjugating L to Z;
conjugating Z to Y;
conjugating Y to X;
wherein if Z is nothing, L is conjugated directly to Y,
if Y is nothing, Z is conjugated directly to X, and
if Y and Z are nothing, L is conjugated directly to X,
thereby preparing a compound represented by the structure of the general formula (A).

In some embodiments, the invention provides processes for the preparation of a compound represented by the structure of the general formula (I):

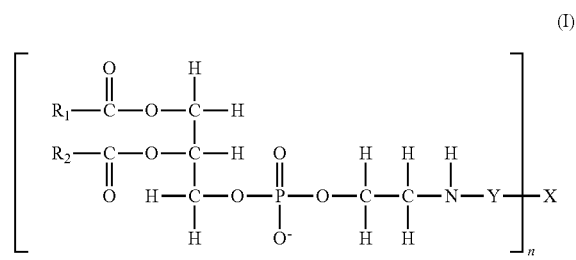

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms;

X is either a physiologically acceptable monomer, dimer, oligomer or a physiologically acceptable polymer, wherein X is a glycosaminoglycan; and n is a number from 1 to 1,000;

wherein if Y is nothing the phosphatidylethanolamine is directly linked to X via an amide bond and if Y is a spacer, the spacer is directly linked to X via an amide or an esteric bond and to the phosphatidylethanolamine via an amide bond, including, inter alia, the steps of:

conjugating the phosphatidylethanolamine to Y; and conjugating Y to X;

if Y is nothing, the phosphatidylethanolamine is conjugated directly to X, thereby preparing a compound represented by the structure of the general formula (I).

In some embodiments of the invention, the phosphatidylethanolamine is the chemical moiety represented by the structure of:

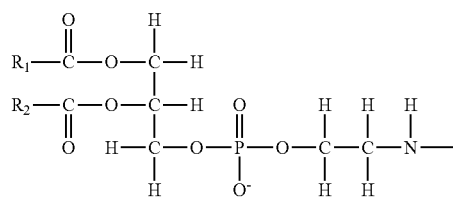

wherein $R_1$ and $R_2$ are defined herein.

In some embodiments, the invention provides processes for the preparation of a compound represented by the structure of the general formula (II):

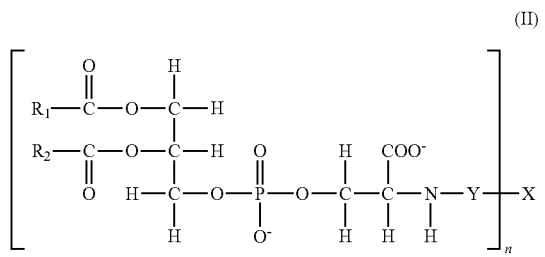

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms;

X is a physiologically acceptable monomer, dimer, oligomer or polymer wherein x is a glycosaminoglycan; and n is a number from 1 to 1000;

wherein if Y is nothing the phosphatidylserine is directly linked to X via an amide bond and if Y is a spacer, the spacer is directly linked to X via an amide or an esteric bond and to the phosphatidylserine via an amide bond, including, inter alia, the steps of:

conjugating the phosphatidylserine to Y;

conjugating Y to X;

if Y is nothing, the phosphatidylserine is conjugated directly to X, thereby preparing a compound represented by the structure of the general formula (II).

In certain embodiments of the invention, the phosphatidylserine is the chemical moiety represented by the structure of:

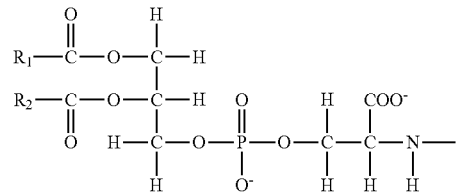

wherein $R_1$ and $R_2$ are defined herein.

In some embodiments, the invention provides processes for the preparation of a compound represented by the structure of the general formula (III):

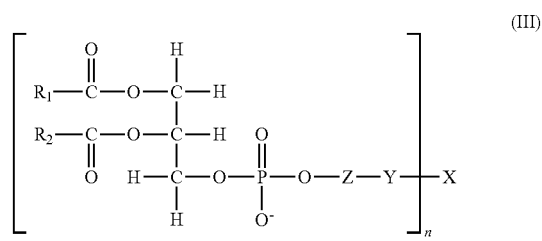

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a physiologically acceptable monomer, dimer, oligomer, or polymer, wherein x is a glycosaminoglycan; and n is a number from 1 to 1000;

wherein any bond between the phosphatidyl, Z, Y and X is either an amide or anesteric bond, including, inter alia, the steps of:

conjugating the phosphatidyl to Z;

conjugating Z to Y;

conjugating Y to X;

wherein if Z is nothing, the phosphatidyl is conjugated directly to Y, if Y is nothing, Z is conjugated directly to X, and if Y and Z are nothing, the phosphatidyl is conjugated directly to X, thereby preparing a compound represented by the structure of the general formula (III).

In some embodiments of the invention, the phosphatidyl may be the chemical moiety represented by the structure of:

$$R_1-\overset{O}{\underset{\|}{C}}-O-\overset{H}{\underset{|}{C}}-H$$
$$R_2-\overset{\|}{\underset{O}{C}}-O-\overset{|}{\underset{|}{C}}-H \quad \overset{O}{\underset{\|}{}}$$
$$H-\overset{|}{\underset{|}{C}}-O-\overset{\|}{\underset{|}{P}}-O-$$
$$H \quad O^-$$

wherein $R_1$ and $R_2$ are defined herein.

In some embodiments, the invention provides processes for the preparation of a compound represented by the structure of the general formula (IV):

$$\left[ \begin{array}{c} R_1-\overset{H}{\underset{|}{C}}-H \\ R_2-\overset{\|}{\underset{O}{C}}-O-\overset{|}{\underset{|}{C}}-H \quad \overset{O}{\underset{\|}{}} \\ H-\overset{|}{\underset{|}{C}}-O-\overset{\|}{\underset{|}{P}}-O-Z-Y \\ H \quad O^- \end{array} \right]_n -X \quad \text{(IV)}$$

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a physiologically acceptable monomer, dimer, oligomer, or polymer, wherein x is a glycosaminoglycan; and n is a number from 1 to 1000;

wherein any bond between the phospholipid, Z, Y and X is either an amide or an esteric bond, including, inter alia, the steps of:

conjugating the phospholipid to Z;

conjugating Z to Y;

conjugating Y to X;

wherein if Z is nothing, the phospholipid is conjugated directly to Y, if Y is nothing, Z is conjugated directly to X, and if Y and Z are nothing, the phospholipid is conjugated directly to X, thereby preparing a compound represented by the structure of the general formula (IV).

In some embodiments of the invention, the phospholipid may be the chemical moiety represented by the structure of:

$$R_1-\overset{H}{\underset{|}{C}}-H$$
$$R_2-\overset{\|}{\underset{O}{C}}-O-\overset{|}{\underset{|}{C}}-H \quad \overset{O}{\underset{\|}{}}$$
$$H-\overset{|}{\underset{|}{C}}-O-\overset{\|}{\underset{|}{P}}-O-$$
$$H \quad O^-$$

wherein $R_1$ and $R_2$ are defined herein.

In some embodiments, the invention provides processes for the preparation of a compound represented by the structure of the general formula (V):

$$\left[ \begin{array}{c} R_1-\overset{O}{\underset{\|}{C}}-O-\overset{H}{\underset{|}{C}}-H \\ R_2-\overset{|}{\underset{|}{C}}-H \quad \overset{O}{\underset{\|}{}} \\ H-\overset{|}{\underset{|}{C}}-O-\overset{\|}{\underset{|}{P}}-O-Z-Y \\ H \quad O^- \end{array} \right]_n -X \quad \text{(V)}$$

wherein $R_1$ is a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a physiologically acceptable monomer, dimer, oligomer, or polymer, wherein x is a glycosaminoglycan; and n is a number from 1 to 1000;

wherein any bond between the phospholipid, Z, Y and X is either an amide or an esteric bond, including, inter alia, the steps of:

conjugating the phospholipid to Z;

conjugating Z to Y;

conjugating Y to X;

wherein if Z is nothing, the phospholipid is conjugated directly to Y, if Y is nothing, Z is conjugated directly to X, and if Y and Z are nothing, the phospholipid is conjugated directly to X, thereby preparing a compound represented by the structure of the general formula (V).

In some embodiments of the invention, the phospholipid may be the chemical moiety represented by the structure of:

$$R_1-\overset{O}{\underset{\|}{C}}-O-\overset{H}{\underset{|}{C}}-H$$
$$R_2-\overset{|}{\underset{|}{C}}-H \quad \overset{O}{\underset{\|}{}}$$
$$H-\overset{|}{\underset{|}{C}}-O-\overset{\|}{\underset{|}{P}}-O-$$
$$H \quad O^-$$

wherein $R_1$ and $R_2$ are defined herein.

In some embodiments, the invention provides processes for the preparation of a compound represented by the structure of the general formula (VI):

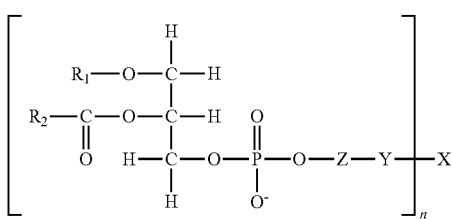

(VI)

wherein
$R_1$ is either hydrogen or a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Z is either nothing, inositol, choline, or glycerol;
Y is either nothing or a spacer group ranging in length from 2 to 30 atoms;
X is a physiologically acceptable monomer, dimer, oligomer, or polymer, wherein x is a glycosaminoglycan; and
n is a number from 1 to 1000;
wherein any bond between the phospholipid, Z, Y and X is either an amide or an esteric bond,
including, inter alia, the steps of:
conjugating the phospholipid to Z;
conjugating Z to Y;
conjugating Y to X;
wherein if Z is nothing, the phospholipid is conjugated directly to Y,
if Y is nothing, Z is conjugated directly to X, and
if Y and Z are nothing, the phospholipid is conjugated directly to X, thereby preparing a compound represented by the structure of the general formula (VI).

In some embodiments of the invention, the phospholipid may be the chemical moiety represented by the structure of:

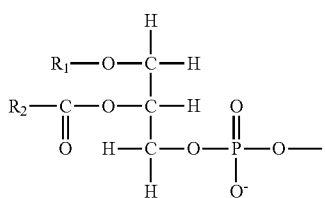

wherein $R_1$ and $R_2$ are defined herein.

In some embodiments, the invention provides processes for the preparation of a compound represented by the structure of the general formula (VII):

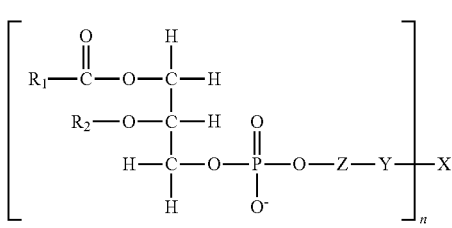

(VII)

wherein
$R_1$ is a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, inositol, choline, or glycerol;
Y is either nothing or a spacer group ranging in length from 2 to 30 atoms;
X is a physiologically acceptable monomer, dimer, oligomer, or polymer, wherein x is a glycosaminoglycan; and
n is a number from 1 to 1000;
wherein any bond between the phospholipid, Z, Y and X is either an amide or an esteric bond,
including, inter alia, the steps of:
conjugating the phospholipid to Z;
conjugating Z to Y;
conjugating Y to X;
wherein if Z is nothing, the phospholipid is conjugated directly to Y,
if Y is nothing, Z is conjugated directly to X, and
if Y and Z are nothing, the phospholipid is conjugated directly to X, thereby preparing a compound represented by the structure of the general formula (VII).

In some embodiments of the invention, the phospholipid may be the chemical moiety represented by the structure of:

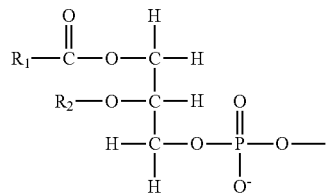

wherein $R_1$ and $R_2$ are defined herein.

In some embodiments, the invention provides processes for the preparation of a compound represented by the structure of the general formula (VIII):

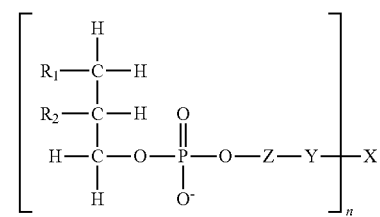

(VIII)

wherein
$R_1$ is a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer, wherein x is a glycosaminoglycan; and n is a number from 1 to 1000;
wherein any bond between the phospholipid, Z, Y and X is either an amide or an esteric bond,
including, inter alia, the steps of:
conjugating the phospholipid to Z;
conjugating Z to Y;
conjugating Y to X;
wherein if Z is nothing, the phospholipid is conjugated directly to Y,
if Y is nothing, Z is conjugated directly to X, and
if Y and Z are nothing, the phospholipid is conjugated directly to X, thereby preparing a compound represented by the structure of the general formula (VIII).

In some embodiments of the invention, the phospholipid may be the chemical moiety represented by the structure of:

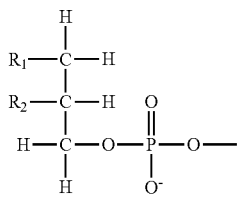

wherein $R_1$ and $R_2$ are defined herein.

In some embodiments, the invention provides processes for the preparation of a compound represented by the structure of the general formula (IX):

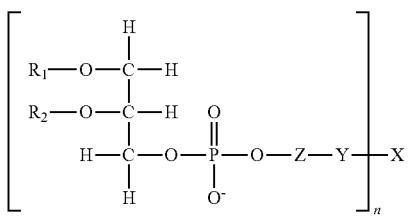

(IX)

wherein
$R_1$ is either hydrogen or a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer, wherein x is a glycosaminoglycan; and
n is a number from 1 to 1000;
wherein any bond between the phospholipid, Z, Y and X is either an amide or an esteric bond,
including, inter alia, the steps of:
conjugating the phospholipid to Z;
conjugating Z to Y;
conjugating Y to X;
wherein if Z is nothing, the phospholipid is conjugated directly to Y,
if Y is nothing, Z is conjugated directly to X, and
if Y and Z are nothing, the phospholipid is conjugated directly to X, thereby preparing a compound represented by the structure of the general formula (IX).

In some embodiments of the invention, the phospholipid may be the chemical moiety represented by the structure of:

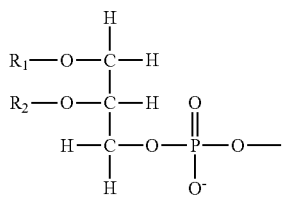

wherein $R_1$ and $R_2$ are defined herein.

In some embodiments, the invention provides processes for the preparation of a compound represented by the structure of the general formula (IXa):

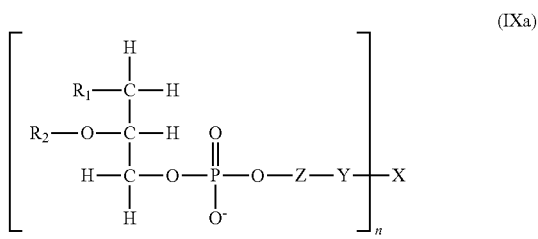

(IXa)

wherein
$R_1$ is either hydrogen or a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer, wherein x is a glycosaminoglycan; and
n is a number from 1 to 1000;
wherein any bond between the phospholipid, Z, Y and X is either an amide or an esteric bond,
including, inter alia, the steps of:
conjugating the phospholipid to Z;
conjugating Z to Y;
conjugating Y to X;
wherein if Z is nothing, the phospholipid is conjugated directly to Y,
if Y is nothing, Z is conjugated directly to X, and
if Y and Z are nothing, the phospholipid is conjugated directly to X, thereby preparing a compound represented by the structure of the general formula (IXa).

In some embodiments of the invention, the phospholipid may be the chemical moiety represented by the structure of:

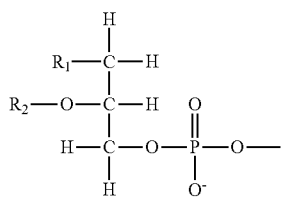

wherein $R_1$ and $R_2$ are defined herein.

In some embodiments, the invention provides processes for the preparation of a compound represented by the structure of the general formula (IXb):

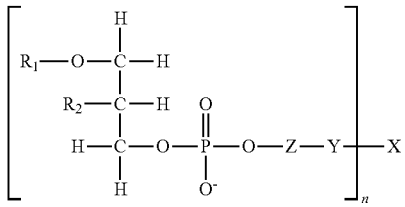

(IXb)

wherein
- $R_1$ is either hydrogen or a linear, saturated, mono-unsaturated, or poly-unsaturated, alkyl chain ranging in length from 2 to 30 carbon atoms;
- $R_2$ is either hydrogen or a linear, saturated, mono-unsaturated, or poly-unsaturated, alkyl chain ranging in length from 2 to 30 carbon atoms;
- Z is either nothing, ethanolamine, serine, inositol, choline, or glycerol;
- Y is either nothing or a spacer group ranging in length from 2 to 30 atoms;
- X is a physiologically acceptable monomer, dimer, oligomer, or polymer, wherein x is a glycosaminoglycan; and
- n is a number from 1 to 1000;
- wherein any bond between the phospholipid, Z, Y and X is either an amide or an esteric bond, including, inter alia, the steps of:
conjugating the phospholipid to Z;
conjugating Z to Y;
conjugating Y to X;
wherein if Z is nothing, the phospholipid is conjugated directly to Y,
if Y is nothing, Z is conjugated directly to X, and
if Y and Z are nothing, the phospholipid is conjugated directly to X, thereby preparing a compound represented by the structure of the general formula (IXb).

In some embodiments of the invention, the phospholipid may be the chemical moiety represented by the structure of:

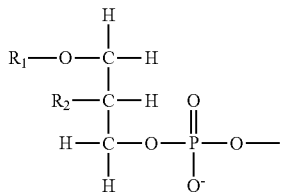

wherein $R_1$ and $R_2$ are defined herein.

In some embodiments, the invention provides processes for the preparation of a compound represented by the structure of the general formula (X):

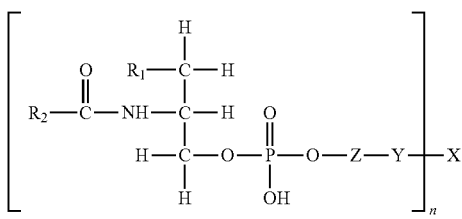

(X)

wherein
- $R_1$ is either hydrogen or a linear, saturated, mono-unsaturated, or poly-unsaturated, alkyl chain ranging in length from 2 to 30 carbon atoms;
- $R_2$ is a linear, saturated, mono-unsaturated, or poly-unsaturated, alkyl chain ranging in length from 2 to 30 carbon atoms;
- Z is either nothing ethanolamine, serine, inositol, choline, or glycerol;
- Y is either nothing or a spacer group ranging in length from 2 to 30 atoms;
- X is a physiologically acceptable monomer, dimer, oligomer, or polymer, wherein x is a glycosaminoglycan; and
- n is a number from 1 to 1000;
- wherein any bond between the ceramide phosphoryl, Z, Y and X is either an amide or an esteric bond, including, inter alia, the steps of: conjugating the ceramide phosphoryl to Z;
conjugating Z to Y;
conjugating Y to X;
wherein if Z is nothing, the ceramide phosphoryl is conjugated directly to Y,
if Y is nothing, Z is conjugated directly to X, and
if Y and Z are nothing, the ceramide phosphoryl is conjugated directly to X, thereby preparing a compound represented by the structure of the general formula (X).

In some embodiments of the invention, the ceramide phosphoryl may be the chemical moiety represented by the structure of:

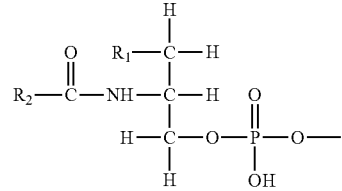

wherein $R_1$ and $R_2$ are defined herein.

In some embodiments, the invention provides processes for the preparation of a compound represented by the structure of the general formula (XI):

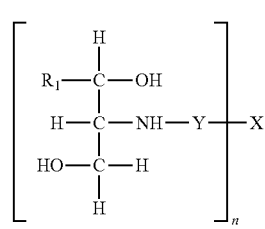

(XI)

wherein
- $R_1$ is a linear, saturated, mono-unsaturated, or poly-unsaturated, alkyl chain ranging in length from 2 to 30 carbon atoms;
- Y is either nothing or a spacer group ranging in length from 2 to 30 atoms;
- X is a physiologically acceptable monomer, dimer, oligomer or polymer, wherein x is a glycosaminoglycan; and
- n is a number from 1 to 1000;
- wherein if Y is nothing the sphingosyl is directly linked to X via an amide bond and if Y is a spacer, the spacer is directly linked to X and to the sphingosyl via an amide bond and to X via an amide or an esteric bond, including, inter alia, the steps of:
conjugating the sphingosyl to Y;
conjugating Y to X;

wherein if Y is nothing, the sphingosyl is conjugated directly to X, thereby preparing a compound represented by the structure of the general formula (XI).

In some embodiments of the invention, the sphingosyl may be the chemical moiety represented by the structure of:

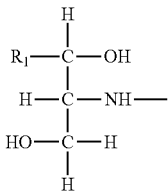

wherein $R_1$ is defined herein.

In some embodiments, the invention provides processes for the preparation of a compound represented by the structure of the general formula (XII):

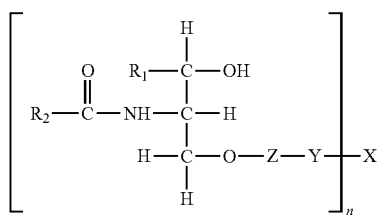

(XII)

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
L is ceramide;
Z is either nothing, ethanolamine, serine, inositol, choline, or glycerol;
Y is either nothing or a spacer group ranging in length from 2 to 30 atoms;
X is a physiologically acceptable monomer, dimer, oligomer or polymer, wherein x is a glycosaminoglycan; and
n is a number from 1 to 1000;
wherein any bond between the ceramide, Z, Y and X is either an amide or an esteric bond, including, inter alia, the steps of:
conjugating the ceramide to Z;
conjugating Z to Y;
conjugating Y to X;
wherein if Z is nothing, the ceramide is conjugated directly to Y,
if Y is nothing, Z is conjugated directly to X, and
if Y and Z are nothing, the ceramide is conjugated directly to X, thereby preparing a compound represented by the structure of the general formula (XII).

In some embodiments of the invention, the ceramide may be the chemical moiety represented by the structure of:

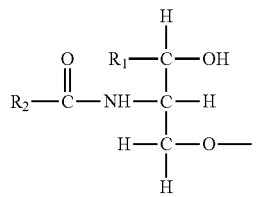

wherein $R_1$ and $R_2$ are defined herein.

In some embodiments, the invention provides processes for the preparation of a compound represented by the structure of the general formula (XIII):

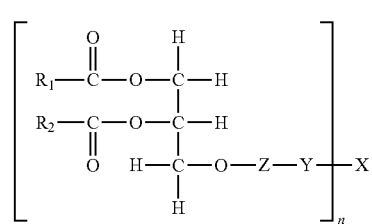

(XIII)

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Z is either nothing, choline, phosphate, inositol, or glycerol;
Y is either nothing or a spacer group ranging in length from 2 to 30 atoms;
X is a physiologically acceptable monomer, dimer, oligomer or polymer, wherein x is a glycosaminoglycan; and
n is a number from 1 to 1000;
wherein any bond between the diglyceryl, Z, Y and X is either an amide or an esteric bond,
including, inter alia, the steps of:
conjugating the diglyceryl to Z;
conjugating Z to Y;
conjugating Y to X;
wherein if Z is nothing, the diglyceryl is conjugated directly to Y,
if Y is nothing, Z is conjugated directly to X, and
if Y and Z are nothing, the diglyceryl is conjugated directly to X, thereby preparing a compound represented by the structure of the general formula (XIII)

In some embodiments of the invention, the diglyceryl may be the chemical moiety represented by the structure of:

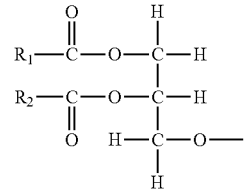

wherein $R_1$ and $R_2$ are defined herein.

In some embodiments, the invention provides processes for the preparation of a compound represented by the structure of the general formula (XIV):

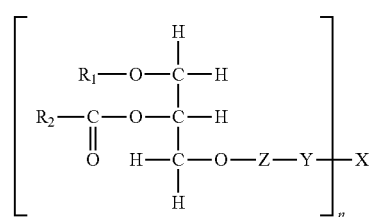

(XIV)

wherein
$R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the glycerolipid, Z, Y and X is either an amide or an esteric bond, including, inter alia, the steps of:

conjugating the glycerolipid to Z;
conjugating Z to Y;
conjugating Y to X;
wherein if Z is nothing, the glycerolipid is conjugated directly to Y,
if Y is nothing, Z is conjugated directly to X, and
if Y and Z are nothing, the glycerolipid is conjugated directly to X, thereby preparing a compound represented by the structure of the general formula (XIV).

In some embodiments of the invention, the glycerolipid may be the chemical moiety represented by the structure of:

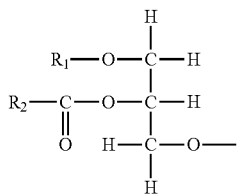

wherein $R_1$ and $R_2$ are defined herein.

In some embodiments, the invention provides processes for the preparation of a compound represented by the structure of the general formula (XV):

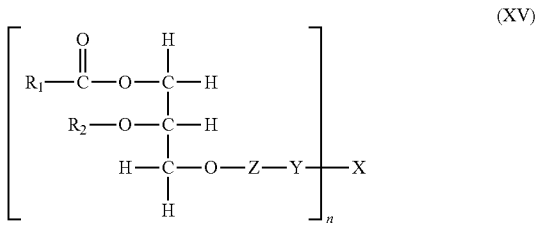

(XV)

wherein $R_1$ is a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the glycerolipid, Z, Y and X is either an amide or an esteric bond, including, inter alia, the steps of:

conjugating the glycerolipid to Z;
conjugating Z to Y;
conjugating Y to X;
wherein if Z is nothing, the glycerolipid is conjugated directly to Y,
if Y is nothing, Z is conjugated directly to X, and
if Y and Z are nothing, the glycerolipid is conjugated directly to X, thereby preparing a compound represented by the structure of the general formula (XV).

In some embodiments of the invention, the glycerolipid may be the chemical moiety represented by the structure of:

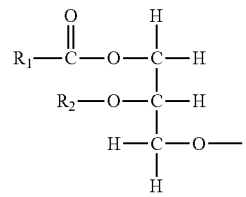

wherein $R_1$ and $R_2$ are defined herein.

In some embodiments, the invention provides processes for the preparation of a compound represented by the structure of the general formula (XVI):

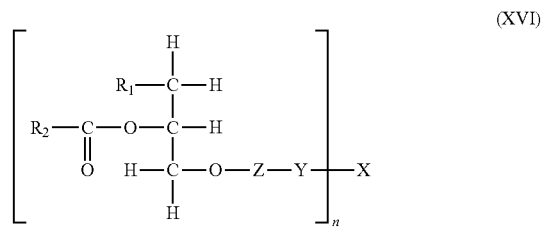

(XVI)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the lipid, Z, Y and X is either an amide or an esteric bond, including, inter alia, the steps of:
conjugating the lipid to Z;
conjugating Z to Y;
conjugating Y to X;
wherein if Z is nothing, the lipid is conjugated directly to Y,
if Y is nothing, Z is conjugated directly to X, and
if Y and Z are nothing, the lipid is conjugated directly to X, thereby preparing a compound represented by the structure of the general formula (XVI).

In some embodiments of the invention, the lipid may be the chemical moiety represented by the structure of:

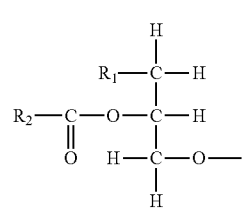

wherein $R_1$ and $R_2$ are defined herein.

In some embodiments, the invention provides processes for the preparation of a compound represented by the structure of the general formula (XVII):

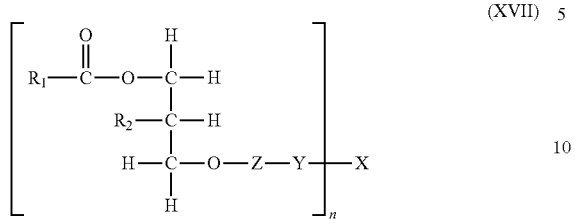

(XVII)

wherein
$R_1$ is either hydrogen or a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Z is either nothing, choline, phosphate, inositol, or glycerol;
Y is either nothing or a spacer group ranging in length from 2 to 30 atoms;
X is a physiologically acceptable monomer, dimer, oligomer or polymer, wherein x is a glycosaminoglycan; and
n is a number from 1 to 1000;
wherein any bond between the lipid, Z, Y and X is either an amide or an esteric bond,
including, inter alia, the steps of:
conjugating the lipid to Z;
conjugating Z to Y;
conjugating Y to X;
wherein if Z is nothing, the lipid is conjugated directly to Y, if Y is nothing, Z is conjugated directly to X, and
if Y and Z are nothing, the lipid is conjugated directly to X, thereby preparing a compound represented by the structure of the general formula (XVII).

In some embodiments of the invention, the lipid may be the chemical moiety represented by the structure of:

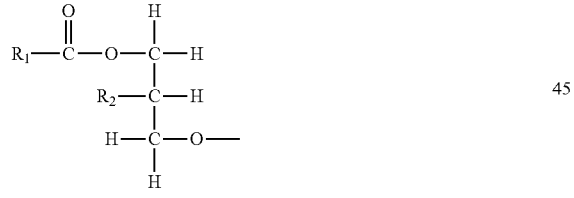

wherein $R_1$ and $R_2$ are defined herein.

In some embodiments, the invention provides processes for the preparation of a compound represented by the structure of the general formula (XVIII):

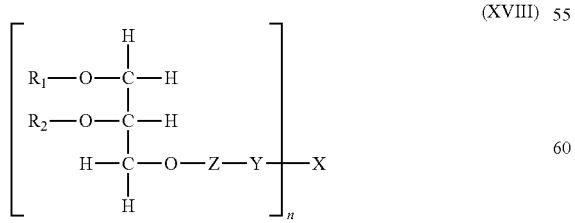

(XVIII)

wherein
$R_1$ is either hydrogen or a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, choline, phosphate, inositol, or glycerol;
Y is either nothing or a spacer group ranging in length from 2 to 30 atoms;
X is a physiologically acceptable monomer, dimer, oligomer or polymer, wherein x is a glycosaminoglycan; and
n is a number from 1 to 1000;
wherein any bond between the lipid, Z, Y and X is either an amide or an esteric bond,
including, inter alia, the steps of:
conjugating the lipid to Z;
conjugating Z to Y;
conjugating Y to X;
wherein if Z is nothing, the lipid is conjugated directly to Y, if Y is nothing, Z is conjugated directly to X, and
if Y and Z are nothing, the lipid is conjugated directly to X, thereby preparing a compound represented by the structure of the general formula (XVIII).

In some embodiments of the invention, the lipid may be the chemical moiety represented by the structure of:

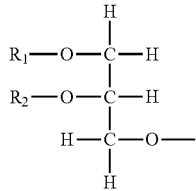

wherein $R_1$ and $R_2$ are defined herein.

In some embodiments, the invention provides processes for the preparation of a compound represented by the structure of the general formula (XIX):

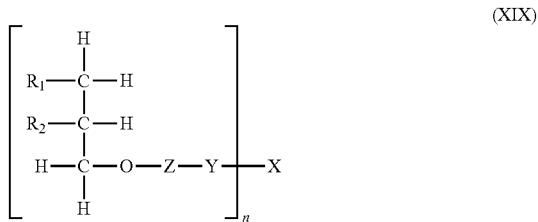

(XIX)

wherein
$R_1$ is either hydrogen or a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, choline, phosphate, inositol, or glycerol;
Y is either nothing or a spacer group ranging in length from 2 to 30 atoms;
X is a physiologically acceptable monomer, dimer, oligomer or polymer, wherein x is a glycosaminoglycan; and
n is a number from 1 to 1000;
wherein any bond between the lipid, Z, Y and X is either an amide or an esteric bond,
including, inter alia, the steps of:
conjugating the lipid to Z;
conjugating Z to Y;
conjugating Y to X;
wherein if Z is nothing, the lipid is conjugated directly to Y, if Y is nothing, Z is conjugated directly to X, and
if Y and Z are nothing, the lipid is conjugated directly to X, thereby preparing a compound represented by the structure of the general formula (XIX).

In some embodiments of the invention, the lipid may be the chemical moiety represented by the structure of:

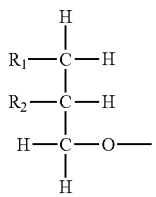

wherein $R_1$ and $R_2$ are defined herein.

In some embodiments, the invention provides processes for the preparation of a compound represented by the structure of the general formula (XX):

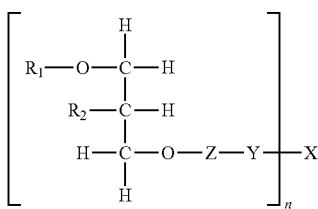

(XX)

wherein
$R_1$ is either hydrogen or a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, choline, phosphate, inositol, or glycerol;
Y is either nothing or a spacer group ranging in length from 2 to 30 atoms;
X is a physiologically acceptable monomer, dimer, oligomer or polymer, wherein x is a glycosaminoglycan; and
n is a number from 1 to 1000;
wherein any bond between the lipid, Z, Y and X is either an amide or an esteric bond,
including, inter alia, the steps of:
conjugating the lipid to Z;
conjugating Z to Y;
conjugating Y to X;
wherein if Z is nothing, the lipid is conjugated directly to Y,
if Y is nothing, Z is conjugated directly to X, and
if Y and Z are nothing, the lipid is conjugated directly to X, thereby preparing a compound represented by the structure of the general formula (XX).

In some embodiments of the invention, the lipid may be the chemical moiety represented by the structure of:

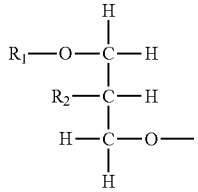

wherein $R_1$ and $R_2$ are defined herein.

In some embodiments, the invention provides processes for the preparation of a compound represented by the structure of the general formula (XXI):

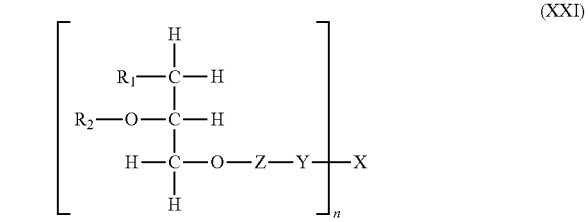

(XXI)

wherein
$R_1$ is either hydrogen or a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, choline, phosphate, inositol, or glycerol;
Y is either nothing or a spacer group ranging in length from 2 to 30 atoms;
X is a physiologically acceptable monomer, dimer, oligomer or polymer, wherein x is a glycosaminoglycan; and
n is a number from 1 to 1000;
wherein any bond between the lipid, Z, Y and X is either an amide or an esteric bond,
including, inter alia, the steps of:
conjugating the lipid to Z;
conjugating Z to Y;
conjugating Y to X;
wherein if Z is nothing, the lipid is conjugated directly to Y,
if Y is nothing, Z is conjugated directly to X, and
if Y and Z are nothing, the lipid is conjugated directly to X, thereby preparing a compound represented by the structure of the general formula (XXI).

In some embodiments of the invention, the lipid may be the chemical moiety represented by the structure of:

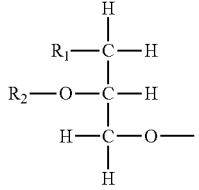

wherein $R_1$ and $R_2$ are defined herein.

In certain embodiments, the conjugating according to the invention may be performed by eliminating a water molecule, thereby forming amide or esteric bonds. In some embodiments, the conjugating may be performed in the presence of a detergent. In some embodiments, the conjugating may be induced by ultrasonic radiation.

In certain embodiments, any compound according to the invention may be prepared by a conjugation process performed by eliminating a water molecule, thereby forming amide or esteric bonds. In some embodiments, any compound according to the invention may be prepared by a conjugation process in the presence of a detergent. In some embodiments, any compound according to the invention may be prepared by a conjugation process induced by ultrasonic radiation.

In certain embodiments of the invention, the conjugation of the phosphatidylethanolamine and chondroitin sulfate is performed in the presence of a detergent. In some of these embodiments the detergent may be, inter alia, DDAB. Of course any other appropriate detergent may be used.

In some embodiments of the invention, the conjugation of the phosphatidylethanolamine and hyaluronic acid is induced by sonication.

Methods of Treating Disease Based on PL Conjugates

In certain embodiments of the invention, the Lipid-conjugates described herein can be used to treat disease, through exerting at least one of their many pharmacological activities, among which are amelioration, or prevention, of tissue injury arising in the course of pathological disease states by stabilizing cell membranes; limiting oxidative damage to cell and blood components; limiting cell proliferation, cell extravasation and (tumor) cell migratory behavior; suppressing immune responses; or attenuating physiological reactions to stress, as expressed in elevated chemokine levels. The medicinal properties of these compounds are readily exemplified in using animal models of the particular disease in which it is desired to use the drug. The patients to whom the lipid or PL conjugates should be administered are those that are experiencing symptoms of disease or who are at risk of contracting the disease or experiencing a recurrent episode or exacerbation of the disease. The efficacy of these compounds in cellular and animal models of disease are described below in The Examples.

The methods of treatment described herein can be used to treat any suitable subject. The term "subject," as used herein, refers to any animal, including but not limited to, any suitable mammal, including primates, such as monkeys and humans, horses, cows, cats, dogs, rabbits, and rodents, such as rats and mice. In certain embodiments, the subject to be treated is human.

The combination of lipids, such as, but not limited to phosphatidylethanolamine and phosphatidylserine, with additional monomer or polymer moieties, is thus a practical route to the production of new drugs for medical purposes, provided that the resultant chemical composition displays the desired range of pharmacological properties. In the cases described herein, the diversity of biological activities and the effectiveness in disease exhibited by the compounds far exceed the properties anticipated by use of the starting materials themselves, when administered alone or in combination. However, it is likely that the PL conjugate compounds, alone or in combination, will prove to be valuable drugs when adapted to methods of disease treatment other than to those conditions specifically described herein.

In certain embodiments, the invention provides methods of treating a subject afflicted with a disease related to allergic rhinitis.

In certain embodiments, the invention provides methods of treating a subject suffering from allergic rhinitis, including, inter alia, the step of administering to a subject an effective amount of a lipid or phospholipid moiety bonded to a physiologically acceptable monomer, dimer, oligomer, or polymer.

In certain embodiments, the invention provides methods of preventing allergic rhinitis in a subject, including, inter alia, the step of administering to a subject an effective amount of a lipid or phospholipid moiety bonded to a physiologically acceptable monomer, dimer, oligomer, or polymer.

In certain embodiments, the invention provides a use of a lipid or phospholipid moiety bonded to a physiologically acceptable monomer, dimer, oligomer, or polymer, in the preparation of a pharmaceutical composition for treating a subject suffering from allergic rhinitis.

In certain embodiments, the invention provides a use of a lipid or phospholipid moiety bonded to a physiologically acceptable monomer, dimer, oligomer, or polymer, in the preparation of a pharmaceutical composition for preventing allergic rhinitis in a subject.

In some embodiments of the invention, the treatment requires controlling the expression, production, and activity of phospholipase enzymes. In some embodiments, the treatment requires controlling the production and/or action of lipid mediators. In some embodiments, the treatment requires amelioration of damage to glycosaminoglycans (GAG) and proteoglycans. In some embodiments, the treatment requires controlling the production and action of oxidants, oxygen radicals and nitric oxide. In some embodiments, the treatment requires anti-oxidant therapy. In some embodiments, the treatment requires anti-endotoxin therapy. In some embodiments, the treatment requires controlling the expression, production or action of cytokines, chemokines, adhesion molecules or interleukines. In some embodiments, the treatment requires protection of lipoproteins from damaging agents. In some embodiments, the treatment requires controlling the proliferation of cells. In some embodiments, the treatment requires controlling of angiogenesis and organ vascularization. In some embodiments, the treatment requires inhibition of invasion-promoting enzymes. In some embodiments, the treatment requires controlling of cell invasion. In some embodiments, the invading cells are white blood cells. In some embodiments, the invading cells are cancer cells. In some embodiments, the treatment requires controlling of white cell activation, adhesion or extravasation. In some embodiments, the treatment requires amelioration of ischemia or reperfusion injury. In some embodiments, the treatment requires inhibition of lymphocyte activation. In some embodiments, the treatment requires protection of blood brain barrier. In some embodiments, the treatment requires control of neurotransmitter production and action. In some embodiments, the treatment requires controlling of blood vessel and airway contraction. In some embodiments, the treatment requires extracorporeal tissue preservation.

In certain embodiments of the invention, the lipid mediator is a glycerolipid. In some embodiments, the lipid mediator is a phospholipid. In some embodiments, the lipid mediator is sphingolipid. In some embodiments, the lipid mediator is a sphingosine. In some embodiments, the lipid mediator is ceramide. In some embodiments, the lipid mediator is a fatty acid. In some embodiments, the fatty acid is arachidonic acid. In some embodiments, the lipid mediator is an arachidonic acid-derived eicosanoid. In some embodiments, the lipid mediator is a platelet activating factor (PAF). In some embodiments, the lipid mediator is a lysophospholipid.

In certain embodiments of the invention, the damaging agent is a phospholipase. In some embodiments, the damaging agent is a reactive oxygen species (ROS). In some embodiments, the damaging agent is a free radical. In some embodiments, the damaging agent is a lysophospholipid. In some embodiments, the damaging agent is a fatty acid or a derivative thereof. In some embodiments, the damaging agent is hydrogen peroxide. In some embodiments, the damaging agent is a phospholipid. In some embodiments, the damaging agent is an oxidant. In some embodiments, the damaging agent is a cationic protein. In some embodiments, the damaging agent is a streptolysin. In some embodiments, the damaging agent is a protease. In some embodiments, the damaging agent is a hemolysin. In some embodiments, the damaging agent is a sialidase.

In certain embodiments of the invention, the invasion-promoting enzyme is collagenase. In some embodiments, the invasion-promoting enzyme is matrix-metaloproteinase (MMP). In some embodiments, the invasion-promoting enzyme is heparinase. In some embodiments, the invasion-promoting enzyme is heparanase. In some embodiments, the invasion-promoting enzyme is hyaluronidase. In some embodiments, the invasion-promoting enzyme is gelatinase. In some embodiments, the invasion-promoting enzyme is chondroitinase. In some embodiments, the invasion-promoting enzyme is dermatanase. In some embodiments, the invasion-promoting enzyme is keratanase. In some embodiments, the invasion-promoting enzyme is protease. In some embodiments, the invasion-promoting enzyme is lyase. In some embodiments, the invasion-promoting enzyme is hydrolase. In some embodiments, the invasion-promoting enzyme is a glycosaminoglycan degrading enzyme. In some embodiments, the invasion-promoting enzyme is a proteoglycan degrading enzyme.

In certain embodiments of the invention, the physiologically acceptable monomer is salicylate. In some embodiments, the physiologically acceptable monomer is salicylic acid. In some embodiments, the physiologically acceptable monomer is aspirin. In some embodiments, the physiologically acceptable monomer is a monosaccharide. In some embodiments, the physiologically acceptable monomer is lactobionic acid. In some embodiments, the physiologically acceptable monomer is glucoronic acid. In some embodiments, the physiologically acceptable monomer is maltose. In some embodiments, the physiologically acceptable monomer is an amino acid. In some embodiments, the physiologically acceptable monomer is glycine. In some embodiments, the physiologically acceptable monomer is a carboxylic acid. In some embodiments, the physiologically acceptable monomer is an acetic acid. In some embodiments, the physiologically acceptable monomer is a butyric acid. In some embodiments, the physiologically acceptable monomer is a dicarboxylic acid. In some embodiments, the physiologically acceptable monomer is a glutaric acid. In some embodiments, the physiologically acceptable monomer is succinic acid. In some embodiments, the physiologically acceptable monomer is a fatty acid. In some embodiments, the physiologically acceptable monomer is dodecanoic acid. In some embodiments, the physiologically acceptable monomer is didodecanoic acid. In some embodiments, the physiologically acceptable monomer is bile acid. In some embodiments, the physiologically acceptable monomer is cholic acid. In some embodiments, the physiologically acceptable monomer is cholesterylhemmisuccinate.

In certain embodiments of the invention, the physiologically acceptable dimer or oligomer is physiologically acceptable dimer or oligomer is a dipeptide. In some embodiments, the physiologically acceptable dimer or oligomer is a disaccharide. In some embodiments, the physiologically acceptable dimer or oligomer is a trisaccharide. In some embodiments, the physiologically acceptable dimer or oligomer is an oligosaccharide. In some embodiments, the physiologically acceptable dimer or oligomer is an oligopeptide. In some embodiments, the physiologically acceptable dimer or oligomer is a di- or trisaccharide monomer unit of glycosaminoglycans. In some embodiments, the physiologically acceptable dimer or oligomer is hyaluronic acid. In some embodiments, the physiologically acceptable dimer or oligomer is heparin. In some embodiments, the physiologically acceptable dimer or oligomer is heparan sulfate. In some embodiments, the physiologically acceptable dimer or oligomer is keratin. In some embodiments, the physiologically acceptable dimer or oligomer is keratan sulfate. In some embodiments, the physiologically acceptable dimer or oligomer is chondroitin. In some embodiments, the chondroitin is chondoitin sulfate. In some embodiments, the chondroitin is chondoitin-4-sulfate. In some embodiments, the chondroitin is chondoitin-6-sulfate. In some embodiments, the physiologically acceptable dimer or oligomer is dermatin. In some embodiments, the physiologically acceptable dimer or oligomer is dermatan sulfate. In some embodiments, the physiologically acceptable dimer or oligomer is dextran. In some embodiments, the physiologically acceptable dimer or oligomer is polygeline ('Haemaccel'). In some embodiments, the physiologically acceptable dimer or oligomer is alginate, In some embodiments, the physiologically acceptable dimer or oligomer is hydroxyethyl starch (Hetastarch). In some embodiments, the physiologically acceptable dimer or oligomer is ethylene glycol. In some embodiments, the physiologically acceptable dimer or oligomer is carboxylated ethylene glycol.

In certain embodiments of the invention, the physiologically acceptable polymer is a glycosaminoglycan. In some embodiments, the physiologically acceptable polymer is hyaluronic acid. In some embodiments, the physiologically acceptable polymer is heparin. In some embodiments, the physiologically acceptable polymer is heparan sulfate. In some embodiments, the physiologically acceptable polymer is chondroitin. In some embodiments, the chondroitin is chondoitin-4-sulfate. In some embodiments, the chondroitin is chondoitin-6-sulfate. In some embodiments, the physiologically acceptable polymer is keratin. In some embodiments, the physiologically acceptable polymer is keratan sulfate. In some embodiments, the physiologically acceptable polymer is dermatin. In some embodiments, the physiologically acceptable polymer is dermatan sulfate. In some embodiments, the physiologically acceptable polymer is carboxymethylcellulose. In some embodiments, the physiologically acceptable polymer is dextran. In some embodiments, the physiologically acceptable polymer is polygeline ('Haemaccel'). In some embodiments, the physiologically acceptable polymer is alginate. In some embodiments, the physiologically acceptable polymer is hydroxyethyl starch ('Hetastarch'). In some embodiments, the physiologically acceptable polymer is polyethylene glycol. In some embodiments, the physiologically acceptable polymer is polycarboxylated polyethylene glycol.

In certain embodiments of the invention, the lipid or phospholipid moiety is phosphatidic acid. In some embodiments, lipid or phospholipid moiety is an acyl glycerol. In some embodiments, lipid or phospholipid moiety is monoacylglycerol. In some embodiments, lipid or phospholipid moiety is diacylglycerol. In some embodiments, lipid or phospholipid moiety is triacylglycerol. In some embodiments, lipid or phospholipid moiety is sphingosine. In some embodiments, lipid or phospholipid moiety is sphingomyelin. In some embodiments, lipid or phospholipid moiety is ceramide. In some embodiments, lipid or phospholipid moiety is phosphatidylethanolamine. In some embodiments, lipid or phospholipid moiety is phosphatidylserine. In some embodiments, lipid or phospholipid moiety is phosphatidylcholine. In some embodiments, lipid or phospholipid moiety is phosphatidylinositol. In some embodiments, lipid or phospholipid moiety is phosphatidylglycerol. In some embodiments, lipid or phospholipid moiety is an ether or alkyl phospholipid derivative thereof.

In some embodiments, the invention provides methods of treating a subject afflicted with a disease, wherein the treatment of the disease requires controlling phospholipase A2 activities; controlling the production and/or action of lipid mediators, such as eicosanoids, platelet activating factor (PAF) and lyso-phospholipids; amelioration of damage to cell surface glycosaminoglycans (GAG) and proteoglycans; controlling the production of oxygen radicals and nitric oxide; protection of cells, tissues, and plasma lipoproteins from damaging agents, such as reactive oxygen species (ROS) and phospholipases; anti-oxidant therapy; anti-endotoxin therapy; controlling of cytokine, chemokine and interleukine production; controlling the proliferation of cells, including smooth muscle cells, endothelial cells and skin fibroblasts; controlling of angiogenesis and organ vascularization; inhibition of invasion-promoting enzymes, such as collagenase, heparinase, heparanase and hyaluronidase; controlling of cell invasion; controlling of white cell activation, adhesion and extravasation; amelioration of ischemia/reperfusion injury, inhibition of lymphocyte activation; controlling of blood vessel and airway contraction; protection of blood brain barrier; controlling of neurotransmitter (e.g., dopamine) production and action (e.g., acetylcholine); extracorporeal tissue preservation or any combination thereof.

In certain embodiments of the invention, the term "controlling" refers to inhibiting the production and action of the above mentioned factors in order to maintain their activity at the normal basal level and suppress their activation in pathological conditions.

In certain embodiments of the invention, the physiologically acceptable monomer is either a salicylate, salicylic acid, aspirin, a monosaccharide, lactobionic acid, maltose, an amino acid, glycine, carboxylic acid, acetic acid, butyric acid, dicarboxylic acid, glutaric acid, succinic acid, fatty acid, dodecanoic acid, didodecanoic acid, bile acid, cholic acid, cholesterylhemmisuccinate; or wherein the physiologically acceptable dimer or oligomer is a dipeptide, a disaccharide, a trisaccharide, an oligopeptide, or a di- or trisaccharide monomer unit of heparin, heparan sulfate, keratin, keratan sulfate, chondroitin, chondoitin-6-sulfate, chondroitin-4-sulfate, dermatin, dermatan sulfate, dextran, or hyaluronic acid; or wherein the physiologically acceptable polymer is a glycosaminoglycan, polygelin ('haemaccel'), alginate, hydroxyethyl starch (hetastarch), polyethylene glycol, polycarboxylated polyethylene glycol, chondroitin-6-sulfate, chondroitin-4-sulfate, keratin, keratin sulfate, heparan sulfate, dermatin, dermatan sulfate, carboxymethylcellulose, heparin, dextran, or hyaluronic acid.

In certain embodiments of the invention, the lipid moiety is either phosphatidic acid, an acyl glycerol, monoacylglycerol, diacylglycerol, triacylglycerol, sphingosine, sphingomyelin, chondroitin-4-sulphate, chondroitin-6-sulphate, ceramide, phosphatidylethanolamine, phosphatidylserine, phosphatidylcholine, phosphatidylinositol, or phosphatidylglycerol, or an ether or alkyl phospholipid derivative thereof, and the physiologically acceptable monomer or polymer moiety is either aspirin, lactobionic acid, maltose, glutaric acid, polyethylene glycol, carboxymethylcellulose, heparin, dextran, hemacell, hetastarch, or hyaluronic acid.

In certain embodiments, the present invention provides for use of a lipid moiety bonded to a physiologically acceptable monomer, dimer, oligomer, or polymer, in the preparation of a pharmaceutical composition for treating a subject afflicted with allergic rhinitis, chronic rhinosinusitis, nasal polyps, asthma, chronic obstructive pulmonary disease, obstructive respiratory disease, colitis, Crohn's disease, central nervous system insult, multiple sclerosis, contact dermatitis, psoriasis, cardiovascular disease, including prophylaxis for invasive procedures, invasive cellular proliferative disorders, anti-oxidant therapy, hemolytic syndromes, sepsis, acute respiratory distress syndrome, tissue transplant rejection syndromes, autoimmune disease, viral infection, and hypersensitivity conjunctivitis.

In certain embodiments, the present invention provides for use of a pharmaceutical composition according to the present invention for treating a subject afflicted with allergic rhinitis, chronic rhinosinusitis, nasal polyps, asthma, chronic obstructive pulmonary disease, obstructive respiratory disease, colitis, Crohn's disease, central nervous system insult, multiple sclerosis, contact dermatitis, psoriasis, cardiovascular disease, including prophylaxis for invasive procedures, invasive cellular proliferative disorders, anti-oxidant therapy, hemolytic syndromes, sepsis, acute respiratory distress syndrome, tissue transplant rejection syndromes, autoimmune disease, viral infection, or hypersensitivity conjunctivitis, wherein the composition is prepared for administration by topical, oral, nasal, aerosol, intravenous, intraocular, intraarterial, subcutaneous, or suppository routes.

In certain embodiments, the invention provides methods of treating a subject suffering from a disease involving the production and/or action of lipid mediators and/or impairment of glycosaminoglycan (GAG) functioning.

In certain embodiments of the invention, the physiologically acceptable monomer may be, inter alia, a salicylate, salicylic acid, aspirin, a monosaccharide, lactobionic acid, glucoronic acid, maltose, amino acid, glycine, carboxylic acid, acetic acid, butyric acid, dicarboxylic acid, glutaric acid, succinic acid, fatty acid, dodecanoic acid, didodecanoic acid, bile acid, cholic acid, cholesterylhemmisuccinate, or wherein the physiologically acceptable dimer or oligomer may be, inter alia, a dipeptide, a disaccharide, a trisaccharide, an oligosaccharide, an oligopeptide, or a di- or trisaccharide monomer unit of glycosaminoglcans, hyaluronic acid, heparin, heparan sulfate, keratin, keratan sulfate, chondroitin, chondroitin sulfate, chondroitin-4-sulfate, chondoitin-6-sulfate, dermatin, dermatan sulfate, dextran, polygeline, alginate, hydroxyethyl starch, ethylene glycol, or carboxylated ethylene glycol, or wherein the physiologically acceptable polymer may be, inter alia, a glycosaminoglycan, hyaluronic acid, heparin, heparan sulfate, chondroitin, chondroitin sulfate, keratin, keratan sulfate, dermatin, dermatan sulfate, carboxymethylcellulose, dextran, polygeline, alginate, hydroxyethyl starch, polyethylene glycol or polycarboxylated polyethylene glycol.

In some embodiments, the physiologically acceptable polymer may be, inter alia, hyaluronic acid.

In some embodiments, the physiologically acceptable polymer may be, inter alia, chondroitin sulfate.

In certain embodiments of the invention, the lipid or phospholipid moiety may be, inter alia, phosphatidic acid, an acyl glycerol, monoacylglycerol, diacylglycerol, triacylglycerol, sphingosine, sphingomyelin, ceramide, phosphatidylethanolamine, phosphatidylserine, phosphatidylcholine, phosphatidylinositol, phosphatidylglycerol, or an ether or alkyl phospholipid derivative thereof.

In certain embodiments, the phospholipid moiety may be, inter alia, phosphatidylethanolamine.

Dosages and Routes of Administration

The methods according to certain embodiments of this invention can be adapted to use of the therapeutic compositions comprising Lipid-conjugates in admixture with conventional excipients, i.e. pharmaceutically acceptable organic or inorganic carrier substances suitable for parenteral, enteral (e.g., oral) or topical application which do not deleteriously react with the active compounds. Suitable pharmaceutically acceptable carriers include but are not limited to water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, white paraffin, glycerol, alginates, hyaluronic acid, collagen, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. They can also be combined where desired with other active agents, e.g., vitamins.

In certain embodiments, pharmaceutical compositions are provided for treating a subject suffering from allergic rhinitis, including a lipid or phospholipid moiety bonded to a physiologically acceptable monomer, dimer, oligomer, or polymer; and a pharmaceutically acceptable carrier or excipient.

In certain embodiments, pharmaceutical compositions are provided for preventing allergic rhinitis in a subject, including a lipid or phospholipid moiety bonded to a physiologically acceptable monomer, dimer, oligomer, or polymer; and a pharmaceutically acceptable carrier or excipient.

In certain embodiments, pharmaceutical compositions are provided for treating a subject suffering from allergic rhinitis, including a lipid or phospholipid moiety bonded to a physiologically acceptable carrier or excipient.

In certain embodiments, pharmaceutical compositions are for preventing allergic rhinitis in a subject, including a lipid or phospholipid moiety bonded to a physiologically acceptable carrier or excipient.

In certain embodiments, pharmaceutical compositions are provided for treating a subject suffering from allergic rhinitis, including any one of the compounds according to the invention or any combination thereof; and a pharmaceutically acceptable carrier or excipient. In certain embodiments, pharmaceutical compositions are provided for preventing allergic rhinitis in a subject, including any one of the compounds according to the invention or any combination thereof; and a pharmaceutically acceptable carrier or excipient.

In certain embodiments, the compounds according to the invention include, inter alia, the compounds represented by the structures of the general formulae: (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII) or any combination thereof.

While the examples provided herein describe use of the PL conjugates in subcutaneous, intraperitoneal or topical administration, the success described affords good evidence to suppose that other routes of administration, or combinations with other pharmaceutical preparations, would be at least as successful. The route of administration (e.g., topical, parenteral, enteral, intravenous, vaginal, inhalation, nasal aspiration (spray), supository or oral) and the dosage regimen will be determined by skilled clinicians, based on factors such as exact nature of the condition being treated, the severity of the condition, the age and general physical condition of the patient, and so on.

In general, the doses utilized for the above described purposes will vary, but will be in an effective amount to exert the desired anti-disease effect. As used herein, the term "pharmaceutically effective amount" refers to an amount of a compound of formulae A and I-XXI which will produce the desired alleviation in symptoms or signs of disease in a patient. The doses utilized for any of the above-described purposes will generally be from 1 to about 1000 milligrams per kilogram of body weight (mg/kg), administered one to four times per day, or by continuous IV infusion. When the compositions are dosed topically, they will generally be in a concentration range of from 0.1 to about 10% w/v, administered 1-4 times per day.

As used herein, the term "pharmaceutically acceptable carrier" refers to any formulation which is safe, and provides the appropriate delivery for the desired route of administration of an effective amount of at least one compound of the present invention. As such, all of the above-described formulations of the present invention are hereby referred to as "pharmaceutically acceptable carriers." This term refers to as well the use of buffered formulations wherein the pH is maintained at a particular desired value, ranging from pH 4.0 to pH 9.0, in accordance with the stability of the compounds and route of administration.

For parenteral application, particularly suitable are injectable, sterile solutions, preferably oily or aqueous solutions, as well as suspensions, emulsions, or implants, including suppositories. Ampoules are convenient unit dosages.

For application by inhalation, particularly for treatment of airway obstruction or congestion, solutions or suspensions of the compounds mixed and aerosolized or nebulized in the presence of the appropriate carrier.

For topical application, particularly for the treatment of skin diseases such as contact dermatitis or psoriasis, admixture of the compounds with conventional creams or delayed release patches is acceptable.

For enteral application, particularly suitable are tablets, dragees, liquids, drops, suppositories, or capsules. A syrup, elixir, or the like can be used when a sweetened vehicle is employed. When indicated, suppositories or enema formulations may be the recommended route of administration.

Sustained or directed release compositions can be formulated, e.g., liposomes or those wherein the active compound is protected with differentially degradable coatings, e.g., by microencapsulation, multiple coatings, etc. It is also possible to freeze-dry the new compounds and use the lyophilisates obtained, for example, for the preparation of products for injection.

Thus, embodiments of the present invention provides for use of the Lipid-conjugates in various dosage forms suitable for nasal, aerosol, rectal, vaginal, conjunctival, intravenous, intra-arterial, and sublingual routes of administration.

It will be appreciated that the actual preferred amounts of active compound in a specific case will vary according to the specific compound being utilized, the particular compositions formulated, the mode of application, and the particular situs and organism being treated. Dosages for a given host can be determined using conventional considerations, e.g., by customary comparison of the differential activities of the subject compounds and of a known agent, e.g., by means of an appropriate, conventional pharmacological protocol.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The main abbreviations used in the application are:
HA=hyaluronic acid
HYPE=dipalmitoyl-phosphatidyl-ethanolamine (PE) conjugated to HA (also referred to as HyPE, HyalPE)

CSA=chondroitin sulfate A
CSAPE=PE conjugated to CSA (also referred to as CsAPE, CsaPE)
CMC=carboxymethyl cellulose
CMPE=PE conjugated to CMC
HEPPE=PE conjugated to heparin (also referred to as HepPE, HePPE)
DEXPE=PE conjugated to dextran
AsPE=PE conjugates to aspirin
HemPE=PE conjugated to Polygeline (haemaccel)
HyDMPE=dimyristoyl PE linked to HA.

Examples demonstrating the utility of lipid-conjugates in preventing and treating disease are presented in PCT/US05/06591 filed 2 Mar. 2005, U.S. application Ser. No. 10/989,606 filed 17 Nov. 2004 and U.S. application Ser. No. 10/989,607 filed 17 Nov. 2004, which are incorporated herein by reference in their entirety.

EXAMPLE 1

A Two-Arm Study to Examine the Safety, Tolerability, and Efficacy of Multiple Intranasal Doses of HyPE on the Response to Nasal Antigen in Allergic Rhinitis Participants Outside of the Allergy Season Overall Study Design Described in this example is a Phase 2, single center, 2-armed study in participants with allergic rhinitis (AR) (See FIG. 1). Participants in Arm 1 were enrolled in a double-blind, placebo-controlled, randomized study evaluating the safety, tolerability, and efficacy of 2% HyPE (Drug or "MRX-4") when administered intra-nasally BID for 6 days. Participants in Arm 2 underwent the same procedures and treatment regime, but received an intranasal steroid in a single-blind fashion. Participants in both arms were blinded at all times to their treatment assignment. All participants underwent a placebo lead-in period (Days 1 to 7) prior to receiving their assigned treatment.

A placebo group was included in Arm 1 (a vehicle composed of isotonic PBS with benzyl alcohol as the preservative) to control for environmental changes (pollen). An intranasal corticosteroid arm (INS) (single blinded) was included to provide a positive control for prevention of symptoms, nasal inflammation and mediator release following NAC (Nasal Antigen Challenge). Drug and placebo were given BID, at approximately 8:00 am and 8:00 pm, using a multiple dose nasal applicator. Eligible participants were randomized in a 1:1 ratio (Drug:Placebo) in the double-blind portion of the study. Once enrolment in Arm 1 had been completed (70 participants had been enrolled), 35 participants were enrolled in Arm 2 (Table 1.1).

TABLE 1.1

Treatment Groups

| Treatment Group | | Days 1 to 7 | Days 15 to 21 |
|---|---|---|---|
| Arm 1 | Group 1 (n = 35) | Placebo (Vehicle) | Drug (2.0% HyPE) |
| | Group 2 (n = 35) | Placebo (Vehicle) | Placebo (a vehicle composed of isotonic PBS with benzyl alcohol as the preservative) |
| Arm 2 | (Group 3, n = 35) | Placebo (Vehicle) | Steroid (Rhinocort [budesonide], 32 µg) |

Indication and Main Criteria for Inclusion:

Healthy adult males and females between 18 and 65 years old, with a history of summer grass pollen allergic rhinitis for at least 2 years, confirmed by a positive skin prick test to Bermuda or Rye grass pollen extract, defined as a ≥3 mm wheal compared with the negative control. Participants must not have used any oral or intranasal, prescription or over-the-counter, anti-allergy medication within the previous 4 weeks or immunotherapy in the previous 3 months. Participants were studied outside of the grass pollen season.

Treatments Administered

HyPE for intranasal administration was provided in an intranasal spray bottle suitable for the administration of multiple doses over the treatment period. Placebo (a vehicle composed of isotonic PBS with benzyl alcohol as the preservative) was provided in a matching multi-dose intranasal spray for the double-blind portion of the study. The steroid used was commercially-available INS, budesonide aqueous spray (Rhinocort®, AstraZeneca)

HyPE was administered intranasally as a 2% HyPE concentration in phosphate-buffered saline (PBS) with benzyl alcohol as a preservative. The solution was placed in glass bottles and closed with the Valois Equadel nasal spray device. Each activation of the nasal applicator delivered 100 µL of solution; resulting in a total dose of 200 µL (1 spray in each nostril) to provide 4 mcg. Rhinocort was administered intranasally 2 sprays BID at a dose of 32 µg per spray (total daily dose 256 µg/day)

Duration of Treatment:

The study consisted of 2 treatment weeks, separated by 1 week of wash-out. Including up to 6 weeks of screening and 4 weeks of follow-up, the entire study could last up to approximately 12 weeks. Participants were required to visit the clinic up to 8 times, including 2 full days (as an outpatient) during which they had the NAC followed by nasal lavage procedures.

All treatments were self-administered. In Arm 1, Drug and placebo were administered using the same type of intranasal applicator, which provided 100 µL of solution to each nostril BID, resulting in a 200 µL dose BID. In Arm 2, Rhinocort 32 µg was administered as 2 sprays BID. The timing of the treatments were as follows (FIG. 1):

Days 1 to 7 (placebo run-in): all participants received placebo (isotonic strength PBS with benzyl alcohol) BID at approximately 8:00 am and 8:00 pm.

Days 8 to 14: washout period.

Days 15 to 21: participants received either Drug, INS or placebo BID at approximately 8:00 am and 8:00 pm.

Nasal Lavage

A subset of participants in each treatment group was selected to undergo nasal lavage procedures for the collection of inflammatory mediators from the nose. Nasal lavage was conducted using 6 mL of warm (37° C.) PBS using a 10 mL syringe attached by tubing to a nasal adaptor or olive. Participants were seated in a forward-flexed neck position (60° from the upright) to prevent fluid from reaching the nasopharynx. To ensure adequate washing, the lavage fluid was passed slowly into the nasal cavity and then left to dwell for 30 seconds. The fluid was then flushed and withdrawn back into the syringe approximately 30 times in 2 minutes until turbid.

The levels of each inflammatory mediator measured in the nasal lavage fluid (leukocytes, eosinophils, cytokines and chemokines) and changes from baseline were examined at each time point.

Nasal Antigen Challenge

The Nasal Antigen Challenge (NAC) was performed by administering Bermuda or Rye grass pollen into the nasal cavity as two 100 µL doses using the BiDose applicator. The dose was defined at screening as the lowest concentration which elicited a positive reaction during a previously administered skin prick test.

Criteria for Evaluation:

Safety: Safety variables were summarized for each dose level and overall. Safety variables included adverse events (AEs), laboratory tests, vital signs (oral body temperature, systolic and diastolic blood pressures, pulse, and respiratory rate), electrocardiogram results, physical examination findings, and concomitant medications.

Pharmacokinetics: Blood samples for the pharmacokinetic assessment of the serum levels of HyPE were collected on Day 14 (baseline) and on Day 21, immediately after administration of study drug.

Efficacy: Nasal symptoms were recorded at 0, 0.5, 1.5, 2.5, 4.5, 6.5, 8.5, and 24 hours postdose on Days 7 and 21. Symptoms of nasal congestion, rhinorrhea, frontal headache, postnasal drip, sneezing, nasal itch, itching ears/palate and cough were each scored on a scale from 0 to 3 (0=none, 1=mild, 2=moderate, 3=severe symptoms). The primary efficacy endpoint was the total symptom score (TSS) comprised of the following 4 symptoms: nasal congestion, rhinorrhea, sneezing and nasal itch. Thus the TSS at each time point ranged from 0 (no symptoms) to 12 (maximal symptoms). The change in the mean symptom score over each 24 hour period postdose from Day 7 (baseline) and Day 21 (post-treatment) were compared among treatment groups as well as changes in clinical improvement as measured by population shift.

Secondary efficacy endpoints included change from baseline in the mean of each of the 8 individual nasal symptoms over 24 hours. In addition, the levels of each inflammatory mediators (leukocytes, eosinophils, cytokines and chemokines) and changes from baseline were examined at each timepoint in those participants who underwent nasal lavage.

Selection of Allergen Responders During NAC (Post Study Analysis).

Since the primary efficacy analysis was the comparison of TSS after NAC after 6 days of daily dosing with the Drug and placebo, and the fact that, in spite of careful selection of participants and of dose of antigen used during NAC, some participants failed to develop nasal symptoms, making evaluation of the Drug impossible. Accordingly, for the purpose of evaluating efficacy, only those participants that experienced significant symptom levels following NAC at Day 7 (after 6 days of placebo treatment) were included in the primary efficacy analysis.

Participants were selected if at Day 7 (baseline) they reported at least one "moderate" score (≥2) at any time point between 0 hrs and 24 hrs (Oh, 0.5 h, 1.5 h, 2.5 h, 4.5 h, 6.5 h, 8.5 h and 24 h) in at least two of the four clinical categories recorded (nasal congestion, rhinorrhea, sneezing and nasal itch). This generated a sub-population of participants for each of the study arms.

Clinical improvement was determined by population shift analysis: The difference (shift) in the number of participants exhibiting an allergic response on Day 21 versus Day 7 for each treatment arm. This difference may be attributed to the treatment since non-responders had not been included in the analysis.

Adverse Events

The most total, as well as selected specific, number and percentage, of Treatment Emergent Adverse Events (TEAEs) are presented in the Table 1.2.

TABLE 2.2

Treatment Emergent Adverse Events:

| | | Placebo (N = 35) | Drug (N = 35) | INS (N = 35) |
|---|---|---|---|---|
| Total number of participants recording a TEAE | | 16 (46%) | 14 (40%) | 19 (54%) |
| Infections and infestations | Total | 13 (37%) | 9 (26%) | 10 (29%) |
| | Rhinitis | 10 (29%) | 7 (20%) | 8 (23%) |
| | Upper Respiratory Tract Infection | 1 (3%) | 2 (6%) | 2 (6%) |
| Respiratory, Thoracic And Mediastinal Disorders* | Total | 6 (17%), | 4 (11%) | 9 (26%) |
| | Cough | 4 (11%) | 0 | 0 |
| | Postnasal Drip | 2 (6%) | 2 (6%) | 0 |
| | Sneezing | 2 (6%) | 1 (3%) | 1 (3%) |
| Nervous System Disorders | Total | 4 (11%) | 5 (14%) | 9 (26%) |
| | Headache | 4 (11%) | 2 (6%) | 6 (17%) |

2% HyPE given intranasally for 6 days had similar safety and tolerability to placebo with the exception of 2 dropouts (due to low platelet count and forbidden concomitant medication) Interesting observations about 2% HyPE when administered intra-nasally in this study included: (i) decreased cough, (ii) decreased headache, and (iii) decreased need for an asmtha rescue medication (e.g., salbutamol), relative to placebo and comparable to intranasal steroid treatment.

Efficacy Results

Figure 9:
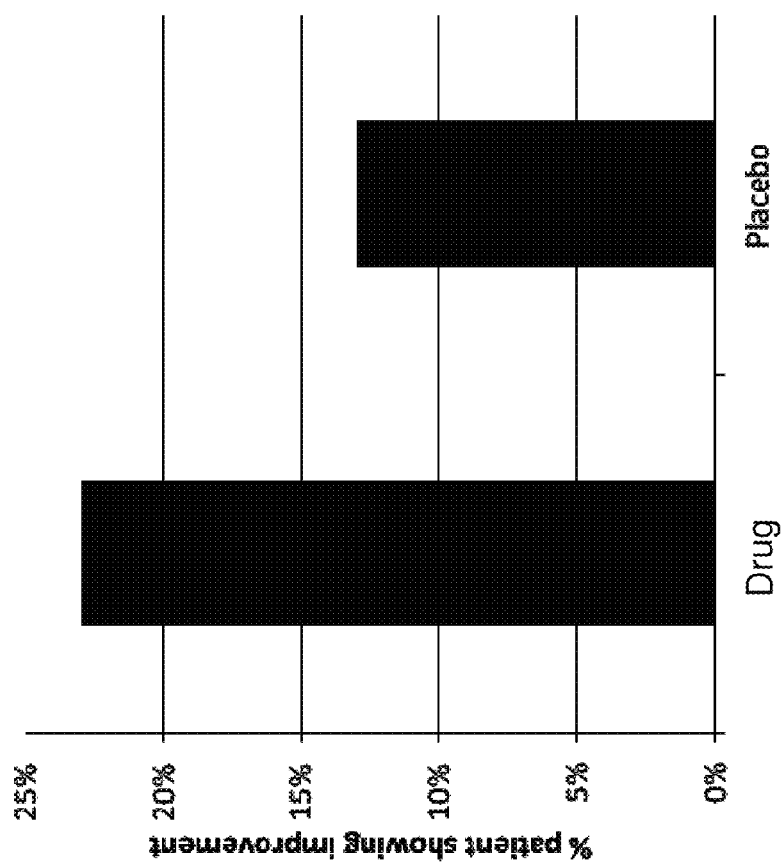
FIG. 9. Bar graph comparing percentage of patients showing symptom improvement between the HyPE (Drug) and Placebo groups.

The primary endpoint was reported for the allergen responder sub-population. Summaries and analysis relating to the clinical improvement (population shift) are presented in in Table 1.3 below and FIG. 9.

TABLE 1.3

Clinical efficacy (population shift) Add n and percentage responders in each of the first two columns

| Group | Allergen responders on Day 7 (% out of FAS) [n = number of participants that responded to NAC on day 7] | Allergen responders on Day 21(%\of allergen responders at Day 7) | Difference (delta n) | Difference in % |
|---|---|---|---|---|
| Control (Day 7 placebo, Day 21 placebo) | 26 (73%) | 23 (89%) | 3 | (11%) |
| Drug (Day 7 placebo, Day 21 Drug) | 28 (80%) | 22 (79%) | 6 | (21%) |
| Steroid (Day 7 placebo, Day 21 steroid) | 23 (66%) | 10 (44%) | 13 | (56%) |

Plots of the mean (normalised) cytokine levels, IL-5, IL-13, MCP-1, TNF-α, IL-8 and eotaxin, and (normalised) eosinophils at Day 21 for the Placebo, MRX-4 and steroid groups are presented in FIGS. 2-8 respectively.

In conclusion, six days of intranasal treatment with 2% HyPE administered intranasally had similar safety and tolerability to placebo with the exception of 2 dropouts (due to low platelet count and forbidden concomitant medication). Furthermore, efficacy analyses showed symptom improvement relative to placebo and approaching intranasal steroid for selected symptoms and inflammatory mediators.

EXAMPLE 2

Toxicity Tests

Experiment 2: The following compounds were tested: HyPE, CMPE, CSAPE and HepPE. The compounds were injected IP at one dose of 1000, 500 or 200 mg/Kg body weight. Toxicity was evaluated after one week, by mortality, body weight, hematocrit, blood count (red and white cells), and visual examination of internal organs after sacrifice. These were compared to control, untreated mice. Each dose was applied to a group of three mice. No significant change in the above criteria was induced by treatment with these compounds, except for the HepPE, which induced hemorrhage.

The non-toxicity of the Lipid conjugates is demonstrated in Table 2.1 and Table 2.2, depicting the results obtained for HyPE in acute (2.1) and long-term (2.2) toxicity tests.

TABLE 2.1

Acute toxicity

| Dose of HyPE (mg/kg body weight) | Body weight (g) | RBC × $10^6$ | WBC × $10^3$ | Hematocrit % |
|---|---|---|---|---|
| 0.0 (control) | 21.9 ± 0.2 | 22.6 ± 0.3 | 10.7 ± 0.4 | 9.3 ± 0.3 | 45.0 ± 0.5 |
| 250 | 22.1 ± 0.4 | 23.1 ± 0.6 | 11.4 ± 0.1 | 7.7 ± 0.2 | 43.3 ± 0.7 |
| 500 | 21.4 ± 0.3 | 22.3 ± 0.4 | 11.5 ± 0.3 | 8.1 ± 1.3 | 44.7 ± 2.3 |
| 1000 | 21.7 ± 0.2 | 22.1 ± 0.2 | 10.9 ± 0.4 | 7.4 ± 0.6 | 40.3 ± 0.7 |

RBC = red blood cells.
WBC = white blood cells.
Each datum is mean ± SEM.

For long-term toxicity test of HyPE, a group of 6 mice received a dose of 100 mg HyPE/Kg body weight, injected IP 3 times a week for 30 weeks (total of 180 mg to a mouse of 20 g). Toxicity was evaluated as for Table 4.1. No mortality, and no significant change in the above criteria was induced by this treatment, compared to normal untreated mice (see Table 4.1), as depicted in Table 2.

TABLE 2.2

Results at week 30:

| | Body weight (g) | RBC × $10^6$ | WBC × $10^3$ | Hematocrit % |
|---|---|---|---|---|
| Control (untreated) rats | 39.5 ± 3.1 | 10.9 ± 0.8 | 9.3 ± 0.6 | 45.0 ± 0.8 |
| HyPE-injected rats | 39.0 ± 2.7 | 11.7 ± 0.7 | 8.1 ± 15 | 43.4 ± 4.9 |

EXAMPLE 3

Synthesis Procedures

The procedures below are examples for synthesis of specific variants of the lipid-conjugates, and can be modified according to the desirable compositions (e.g., changing the molar ratio between the lipid/phospholipid and the GAG, or the GAG size).

Synthesis of low molecular weight lipid-GAG conjugates are prepared according to US publication 2011-0130555 which is incorporated herein by reference.

I. HyPE=phosphatidyl-ethanolamine (PE)-linked hyaluronic acid.
  A. Truncating hyaluronic acid (HA):
    Dissolve 20 g of HA in 12 L water, add 200 mg $FeSO_4.7H_2O$ dissolved in 20 ml water, add 400 ml $H_2O_2$ (30%), stir for 1.5 h. Filter through 30 kD Filtron, Lyophilize. Yield: 16 g truncated HA.
  B. Conjugation with PE (adjusted for 1 g):
  Prepare:
    1. 10 g HA dissolved in 500 ml MES buffer, 0.1 M, pH=6.5
    2. 1.0 g PE dissolved in 500 ml t-BuOH with 100 ml $H_2O$.
  Mix the two solutions, add 1 g HOBT and 10 g EDC. Sonicate the mixture in an ultrasonic bath for 3 h. Remove access free PE (and EDC and HOBT) by extraction into organic phase (by addition of chloroform and methanol to obtain a ratio of $C/M/H_2O$:1/1/1). Separate the aqueous phase by a separation funnel. Repeat this step twice. For final cleaning from reagents, filter through a Filtron membrane (30 kD), and lyophilize.
  Yield: about 8 g.

II. CSAPE=PE-linked chondroitin sulfate A (CSA):
  Prepare:
    1. 10 μCSA dissolved in 1.2 L MES buffer, 0.1 M, pH=6.5
    2. 1 g PE dissolved in 120 ml chloroform/methanol: 1/1. Add 15 ml of a detergent (DDAB).
  Mix 1 with 2, while stirring, add 1 g HOBT and 10 g EDC, continue stirring thoroughly for a day at least. Remove access free PE (and EDC and HOBT) by extraction into organic phase (by addition of chloroform and methanol to obtain a ratio of Chloroform/MeOH/EtOH/$H_2O$: 1/1/0.75/1). Separate the aqueous phase by a separation funnel. Repeat this step twice. Filter through a Filtron membrane (30 kD), and lyophilize. To remove DDAB traces, dissolve 1 g of dry product in 100 ml water and 100 ml MeOH, and clean by ion exchanger using IR120 resin. Dialyse (to remove MeOH) and lyophilize.
  Yield: about 8 g.

Unexpected results showed that the sonication applied in the HyPE synthesis, is an better substitute for the detergent in mixing the aqueous and lipid phases. Using sonication techniques simplifies the synthesis and improves the purification of the product.

It will be appreciated by persons skilled in the art that the present invention is not limited by what has been particularly shown and described herein above and that numerous modifications, all of which fall within the scope of the present invention, exist. Rather, the scope of the invention is defined by the claims which follow:

What is claimed is:

1. A method of treating or preventing allergic rhinitis in a subject, comprising the step of administering to said subject a phospholipid-glycosaminoglycan conjugate represented by the structure of the general formula (A):

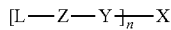

(A)

wherein
L is a phospholipid;
Z is nothing;
Y is nothing;
X is glycosaminoglycan; and
n is a number from 1 to 1000.

2. The method according to claim 1, wherein said glycosaminoglycan is hyaluronic acid.

3. The method according to claim 1, wherein L is phosphatidylethanolamine.

4. The method according to claim 3, wherein said phosphatidylethanolamine is dipalmitoyl phosphatidylethanolamine.

5. The method according to claim 1, wherein treating or preventing allergic rhinitis comprises alleviating or preventing one or more of the symptoms selected from the group consisting of nasal congestion, rhinorrhea, frontal headache, post-nasal drip, sneezing, nasal itch, itching ears/palate and cough.

6. The method according to claim 5, wherein said one or more of the symptoms is selected from the group consisting of nasal congestion, rhinorrhea, sneezing and nasal itch.

7. The method according to claim 5, wherein said one or more of the symptoms comprises headache.

8. The method according to claim 5, wherein said one or more of the symptoms comprises cough.

9. The method according to claim 1, wherein said subject is concurrently taking an asthma rescue medication and said treatment or prevention decreases the subject's need for the asthma rescue medication.

10. The method according to claim 1, wherein the step of administering comprises intranasal administration.

11. The method according to claim 1, wherein the step of administering comprises intranasal administration.

12. The method according to claim 1, wherein treating or preventing allergic rhinitis comprises reducing the levels of a cytokine selected from the group consisting of IL-5, IL-13, MCP-1, TNF-α, IL-8 and eotaxin.

13. The method according to claim 1, wherein treating or preventing allergic rhinitis comprises reducing eosinophil counts.

14. The method according to claim 1, wherein said compound is represented by the structure of the general formula (I):

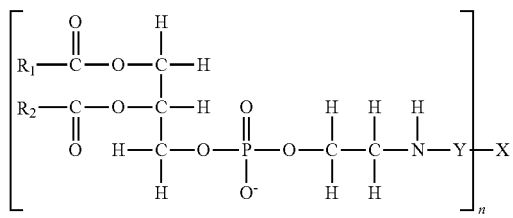

(I)

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Y is nothing;
X is glycosaminoglycan; and
n is a number from 1 to 1,000.

15. The method of claim 1, wherein said glycosaminoglycan is selected from the group consisting of hyaluronic acid, heparin, heparan sulfate, chondrotin sulfate, keratan, keratan sulfate, dermatan sulfate or a derivative thereof.

16. The method of claim 1, wherein said glycosaminoglycan has a molecular weight of between 5 kD and 20 kD.

17. The method of claim 16, wherein said glycosaminoglycan is hyaluronic acid.

* * * * *